United States Patent [19]
Wuonola et al.

[11] Patent Number: 5,668,165
[45] Date of Patent: Sep. 16, 1997

[54] SMALL MOLECULE INHIBITION OF RNA/LIGAND BINDING

[75] Inventors: Mark A. Wuonola, Waltham; Zhe Li, Malden, both of Mass.

[73] Assignee: Scriptgen Pharmaceuticals, Inc., Medford, Mass.

[21] Appl. No.: 475,883

[22] Filed: Jun. 7, 1995

[51] Int. Cl.$^6$ .................. A61K 31/415; C07D 233/64
[52] U.S. Cl. .................. 514/397; 514/232.2; 514/316; 514/333; 514/422; 514/471; 514/438; 514/343; 514/336; 514/235.5; 514/141; 514/326; 514/211; 544/111; 544/129; 546/208; 546/256; 546/187; 546/280.4; 546/283.4; 548/527; 548/315.4; 548/313.1; 548/518; 549/74; 549/491; 540/544; 540/596
[58] Field of Search .................. 548/74, 75, 491, 548/517, 518, 523, 527, 315.4, 313.1; 546/194, 208, 214, 256, 281, 283, 284, 187, 213; 544/129, 146, 141, 152, 111; 514/232.2, 397, 316, 333, 422, 471, 438, 343, 336, 235.5, 141, 326

[56] References Cited

U.S. PATENT DOCUMENTS

| | | | |
|---|---|---|---|
| 4,619,942 | 10/1986 | Tidwell et al. | 514/415 |
| 4,933,347 | 6/1990 | Tidwell et al. | 514/256 |
| 5,463,071 | 10/1995 | Himmelbach et al. | 548/251 |

FOREIGN PATENT DOCUMENTS

WO9530901  11/1995  WIPO.

OTHER PUBLICATIONS

Wilson, W.D. et al Biochemistry 1993, 32(!5), pp. 4098–4104.
Anne, J. et al Antimicrob. Agents Chemother. 1980, 18(2), pp. 231–239.
Jiang, Z. et al Macromolecules 1992, 25(2), pp. 880–882.
Boykin, *J. Med. Chem.*, 20:531, (1977).
Bartel et al., *Cell*, 67:529, (1991).
CDC, MMWR, 35 [20]: 334–339, (1986).
Daly et al., *Biochem.* 32:10497, (1993).
Dann et al., *Liebigs Ann. Chem.*, 160 (1975).
Greenidge et al., *Mol. Pharmacol.* 43:982, (1993).
Harding, R. D., *Trans. R. Soc. Trop Med. Hyg.*, 39:99–124, (1945).
Hope et al., *Proc. National Acad. Sci, USA*, 87:7787–7791, (1990).
Malim et al., *Nature* 338:254, (1989).
Michael et al., *J. Virol.*, 65:1291–1303, (1991).
Napier et al., *Indian Med. Gaz.*, 78:177–183, (1943).
Pomerantz et al., *Cell*, 61:1271–1276, (1990).
Stern et al., *Genes & Development*, 5:2555–2566, (1991).
Von Ahsen et al., *J. Mol. Biol.*, 226:935–41 (1992).
Merck Index [Neamine, amikacin, sisomycin, ribostamycin, butirosin, Kananycin B, Kanamycin A, tobramycin, gentamycin, neomycin B, paromomycin 1, lividomycin A, and hygromycin B] 1939.

Uwe von Ahsen et al., "Non–competitive Inhibition of Group I Intron RNA Self–splicing by Aminoglycoside Antibiotics", J. Mol. Biol., 226:935–941 (1992).

Michael H. Malim et al., "Functional Dissection of the HIV–1 Rev Trans–Activator–Derivation of a Trans–Dominant Repressor of Rev Function", Cell, vol. 58, pp. 205–214, (1989).

Roger J. Pomerantz et al., "Cells Nonproductively Infected with HIV–1 Exhibit an Aberrant Pattern of Viral RNA Expression: A Molecular Model For Latency", Cell, vol. 61, pp. 1271–1276, (1990).

David P. Bartel et al., "HIV–1 Rev Regulation Involves Recognition of Nion–Watson–Crick Base Pairs in Viral RNA", Cell, vol. 67, pp. 529–536, (1991).

Seth Stern et al., "The Herpes simplex virus trans–activator VP16 recognizes the Oct–1 homeo domain: evidence for a homeo domain recognition subdomain", Genes & Development vol. 5, pp. 2555–2566, (1991).

Nelson L. Michael et al., "Induction of Human Immunodeficiency Virus Type 1 Expression in Chronically Infected Cells is Associated Primarily with a Shift in RNA Splicing Patterns", Journal of Virology, 65, pp. 1291–1303, (1991).

Otto Dann et al., "Trypanocide Diamidine mit drei isolierten Ringsystemen", Liebigs Ann. Chem., pp. 160–194, (1975).

Bijan P. Das et al., "Synthesis and Antiprotozoal Activity of 2,5–Bis(4–guanylphenyl)furans", Journal of Med. Chemistry, vol. 20, No. 4, pp. 531–536, (1977).

Paulette A. Greenidge et al., "DNA Minor Groove Recognition Properties of Pentamidine and its Analogs: A Molecular Modeling Study", Molecular Pharmacology, vol. 43, pp. 982–988 (1993).

Constance A. Bell et al., "Structure–Activity Relationships of Pentamidine Analogs against Giardia Lamblia and Correlation of Antigiardial Activity with DNA–Binding Affinity", Antimicrobial Agents and Chemotherapy, 35, pp. 1099–1107, (1991).

David W. Boykin et al., "Dicatiionic Diarylfurans as Anti–Pneumocystis carinii Agents", J. Med. Chem., vol. 38, pp. 912–916, (1995).

W. David Wilson et al., "The Search for Structure–Specific Nucleic Acid–Interactive Drugs: Effects of Compound Structure on RNA versus DNA Interaction Strength", Biochemistry, vol. 32, pp. 4098–4104, (1993).

*Primary Examiner*—C. Warren Ivy
*Assistant Examiner*—Garth M. Dahlen
*Attorney, Agent, or Firm*—Darby & Darby

[57] ABSTRACT

Disclosed is a method for the inhibition of binding of a ligand to an RNA, the inhibition being mediated by a small organic molecule that binds to the RNA, thereby inhibiting ligand binding. A preferred class of small organic molecules are compounds exemplified by 2,5-Bis[3-(2-N,N-dimethylaminopropylamidino)phenyl]furan.

36 Claims, 3 Drawing Sheets

SMALL MOLECULE INHIBITION OF RNA/LIGAND BINDING

FIELD OF THE INVENTION

This invention relates to methods and compositions for inhibiting RNA/ligand interaction, particularly the interaction of the Rev protein of Human Immunodeficiency Virus (HIV) with the Rev-responsive element (RRE) present in HIV-derived messenger RNA molecules.

BACKGROUND OF THE INVENTION

Replication of human retroviruses, such as, for example, human immunodeficiency virus type I (HIV-1), entails an ordered pattern of viral gene expression. This regulated gene expression is dependent upon the sequence-specific interactions of two viral regulatory proteins, Tat and Rev, with their respective sites on viral RNA. Tat is a transcriptional activator, whereas Rev acts posttranscriptionally to increase the cytoplasmic accumulation of the viral gag-pol and env messenger RNAs (mRNAs).

Because Tat and Rev are critical for viral replication they are attractive targets for therapeutic intervention. To date, three strategies have been attempted to reduce the levels of these viral regulatory proteins or to block their action. First, antisense nucleic acids directed against Rev mRNA have been used to decrease the steady-state level of Rev protein. A second strategy is to sequester (titrate) the regulatory protein by the introduction of a large excess of small "decoy" RNA that contains a high affinity protein-binding site. For example, retroviral vectors expressing the Tat-binding site TAR can inhibit viral replication in cultured cells. A third approach is to express dominant negative mutants of the viral regulatory proteins. For example, Rev derivatives bearing mutations within a discrete C-terminal region abolish Rev activity, and these mutants can inhibit wild-type Rev in a cotransfection assay.

A major difficulty inherent in these three strategies is the problem of delivering the therapeutic agent, which is either a nucleic acid or a protein, to target cells within the body. Thus, there is a need in the art for methods and compositions that provide easily deliverable biologically active agents capable of inhibiting the interaction of Rev and/or Tat proteins.

One class of biologically active small organic molecules is the bisamidines, which were known to interact with the minor groove in DNA. Examples of bisamidine compounds include pentamidine and its analogues, which were first developed as antiprotozoal agents (Harding, R. D., *Trans. R. Soc. Trop. Med. Hyg.*, 39:99–124, 1945; Napier et al., *Indian Med. Gaz.*, 78:177–183, 1943) and now are used for the treatment of *Pneumocystis carinii* infections (Greenidge et al., *Mol. Pharmacol.* 43:982, 1993; Tidwell et al., U.S. Pat. No. 4,933,347), and related aromatic amidines useful in inhibiting cell fusion induced by respiratory syncytial virus (Tidwell et al., U.S. Pat. No. 4,619,942). Other 2,5-bis(4-amidinophenyl)furans have been tested for antiprotozoal, particularly antitrypanosomal, activity (Boykin et al., *J. Med. Chem.* 20:531, 1977; Dann et al., *Liebigs Ann. Chem.*, 160, 1975).

SUMMARY OF THE INVENTION

It has now been found that particular classes of small organic molecules can inhibit the binding of a ligand to an RNA, in particular, the binding of the Rev protein of HIV to an RNA molecule containing a Rev-responsive element (RRE).

Successful inhibition of binding of Rev to the high affinity RRE was observed with a class of small organic molecules compounds, Bis-amidine compounds. These compounds have a general formula;

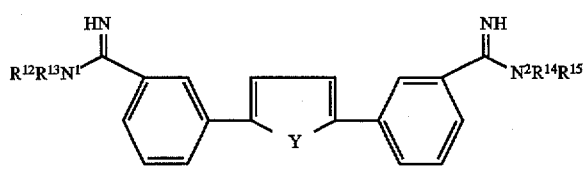

wherein Y is oxygen or sulfur;

$R^{12}$, $R^{13}$, $R^{14}$, and $R^{15}$ are independently selected from the group consisting of hydrogen, $C_1$ to $C_6$ alkyl, aryl, $C_7$ to $C_{12}$ aralkyl, aryloxy, or a heterocyclic ring having 3–10 ring atoms;

wherein the hetero atoms are selected from the group consisting of N, O, S, and any combination thereof; and wherein $R^{12}$, $R^{13}$, $R^{14}$, and $R^{15}$, can be optionally substituted with $C_1$–$C_6$ alkyl, $C_1$–$C_6$ alkoxy, —OH, —SH, amino, $C_1$ to $C_6$ alkylamino, $C_1$ to $C_6$ dialkylamino, arylamino, $C_1$ to $C_6$ alkylarylamino, diarylamino, $C_3$–$C_{10}$ cycloalkyl, $C_3$–$C_8$ cycloalkylamino, $C_3$–$C_8$ dicycloalkylamino, ($C_1$ to $C_6$ alkyl)($C_3$–$C_8$ cycloalkyl) amino, heterocyclic having 5 to about 7 ring atoms wherein the hetero atoms are selected from the group consisting of N, O, S, and any combination thereof.

In addition, $R^{12}$, $R^{13}$, and $N^1$, or $R^{14}$, $R^{15}$, and $N^2$ independently can taken to form a ring; wherein said ring can have from 3 to about 10 ring atoms and optionally one or more hetero atoms selected from the group consisting of nitrogen, oxygen, and sulfur.

Further, $R^{12}$, $R^{13}$, $R^{14}$, and $R^{15}$, can be optionally interrupted by oxygen, nitrogen, sulfur, or any combination thereof; or a pharmaceutically acceptable salt thereof.

The subject invention also contemplates pharmaceutical compositions that incorporate an effective amount of the compounds having the formula as described hereinabove, in conjunction with a pharmaceutically acceptable diluent or carrier.

In another aspect, the invention involves methods to inhibit replication of HIV in an infected cell using the 2,5-Bis(-4-amidinophenyl)furan-derived compounds. The invention also encompasses treatment of HIV infection in humans using the above-described compositions.

DETAILED DESCRIPTION OF THE INVENTION

Figure 1:
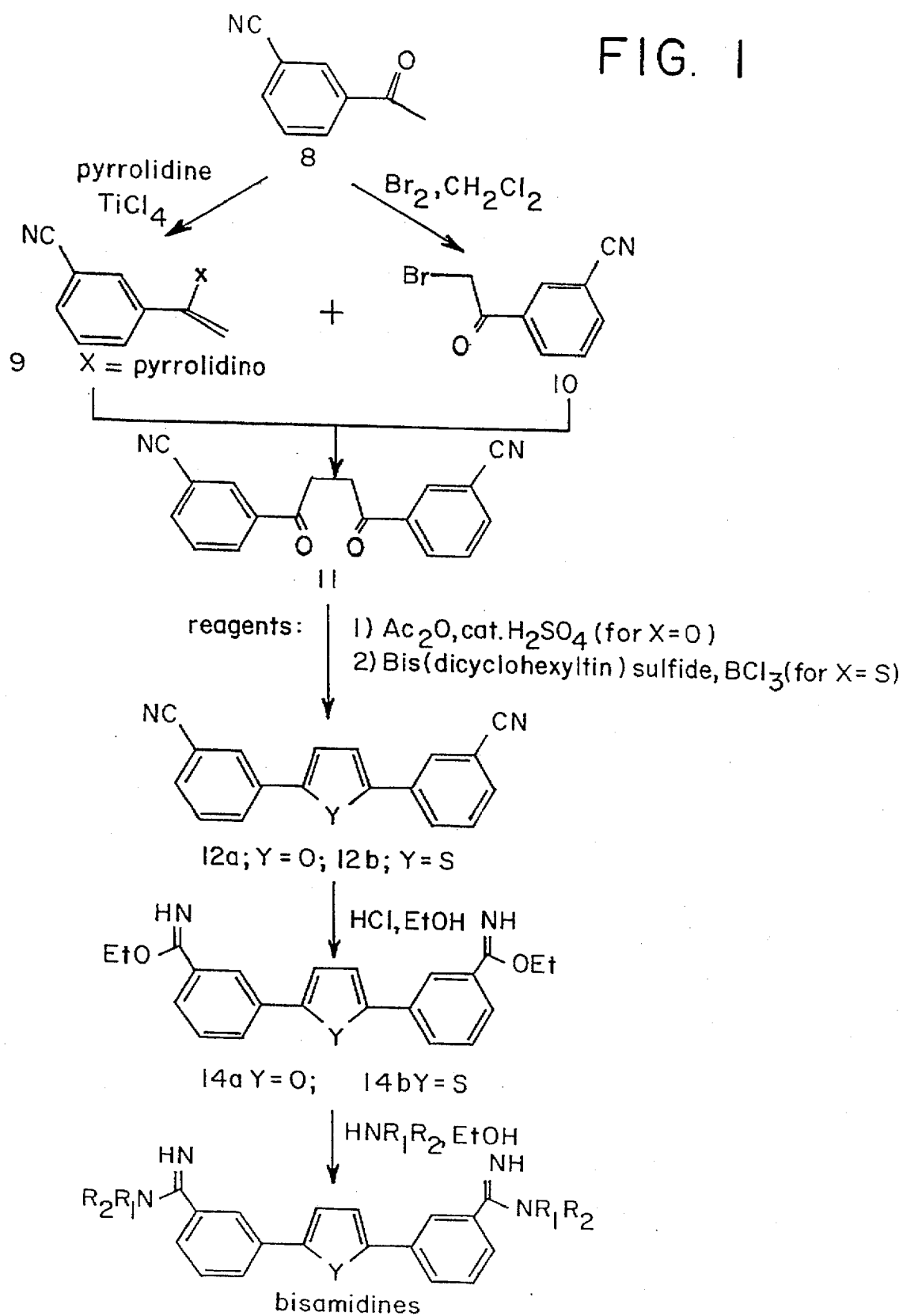
FIG. 1 is a schematic representation of the synthesis of 2,5-Bis(3-amidinophenyl) compounds.

All patents, patent applications, and references referred to herein are hereby incorporated by reference in their entirety.

In the case of inconsistencies, the present disclosure, including definitions, will control.

The present invention is based on the discovery that the specific binding of a ligand to an RNA can be inhibited by the presence of a small organic molecule. The small organic molecule binds to the RNA, thereby inhibiting ligand binding to the RNA. The expression "small organic molecule", as used herein, refers to compounds other than peptides, oligonucleotides, or analogs thereof, and that have molecular weights of less than about 2,000 daltons. The RNA member of the RNA/ligand pair can be any ribonucleic acid polymer. The ligand member of the RNA/ligand pair is preferably a protein, nucleic acid, lipid or carbohydrate.

In a preferred embodiment, the ligand member of the ligand/RNA pair is the HIV Rev protein. The Rev protein acts posttranscriptionally to facilitate the transport of gag-pol and env mRNAs from the nucleus to the cytoplasm of infected cells. Without Rev, these structural gene transcripts fail to accumulate in the cytoplasm, and the virus cannot replicate. A cis-acting element within Rev-responsive transcripts is required for activation by Rev. This element, termed the Rev-responsive element (RRE), has been mapped to a 234 nucleotide fragment (see Malim et al., *Nature* 338:254 (1989)).

Rev binds specifically to the RRE in vitro. In chemical and RNAase protection experiments, binding of Rev primarily protects nucleotides within a 66 nucleotide fragment, referred to as domain II of the RRE. This fragment has been shown to be necessary and sufficient for high affinity Rev binding. Described below are experiments in which small organic molecules were tested for their ability to block Rev binding to a labeled 67-nt high affinity Rev-binding site (see Bartel et al., *Cell* 67: 529 (1991)).

2-Deoxystreptamine Aminoglycosides

Successful inhibition of binding of Rev to the high affinity RRE was observed with one class of small organic molecules, the 2-deoxystreptamine (2-DOS) aminoglycoside class. The 2-DOS class comprises a group of aminoglycosides that are characterized by the presence of a 2-deoxystreptamine nucleus joined by glycosidic linkages to one or more sugar moieties.

Thirteen members of the 2-DOS aminoglycoside class were tested in a Rev/RRE binding inhibition assay. Specifically, the 2-DOS compounds tested were neamine, amikacin, sisomycin, ribostamycin, butirosin, kananycin B, kanamycin A, tobramycin, gentamycin, neomycin B, paromomycin 1, lividomycin A and hygromycin B. The chemical structure of each of these compounds, with the exception of lividomycin A, is provided in *The Merck Index* (Eleventh Edition, Budavai et al. eds., Rahway (1989)). The structure for lividomycin A is provided in the J. Berdi, CRCI Handbook of "Antibiotic Compounds", Volume I (Carbohydrate Antibiotics), CRC Press Inc. Boca Raton, Fla. (1980).

The 2-DOS class of compounds can be divided into subclasses based on structural features. One method for subclassification is based upon the number of sugar moieties attached to the 2-deoxystreptamine nucleus. Another conventional method for subclassification is based upon the position of substituents on the 2-deoxystreptamine nucleus. The table below summarizes the nature of these structural features for each of the 2-DOS compounds tested.

TABLE 1

| 2-DOS Aminoglycoside | Position of 2-DOS Substituents | Number of Sugar Moieties |
|---|---|---|
| Neamine | 4 | 1 |
| Amikacin | 4–6 | 2 |
| Sisomycin | 4–6 | 2 |
| Ribostamycin | 4–5 | 2 |
| Butirosin | 4–5 | 2 |
| Kanamycin B | 4–6 | 2 |
| Kanamycin A | 4–6 | 2 |
| Tobramycin | 4–6 | 2 |
| Gentamycin | 4–6 | 2 |
| Hygromycin B | 5 | 2 |
| Neomycin B | 4–5 | 3 |
| Paromomycin 1 | 4–5 | 3 |
| Lividomycin A | 4–5 | 4 |

Surprisingly, of the thirteen 2-DOS aminoglycosides tested in the Rev/RRE binding inhibition assay, nine were effective in inhibiting the binding of Rev to the RRE (neomycin B, neamine, ribostamycin, lividomycin A, kanamycin B, amikacin, gentamicin C, sisomicin, and tobramycin). Furthermore, three 2-DOS aminoglycosides (neomycin B, tobramycin, and lividomycin A) had exceptional inhibitory potential. These data clearly demonstrate that the 2-DOS aminoglycosides, through complex and yet-to-be-determined structural features, inhibit Rev/RRE binding. Effective 2-DOS aminoglycosides are believed to contain the proper orientation of amino and hydroxyl groups to provide hydrogen bond donors and acceptors for the RNA bases and to provide positively charged amino groups for interaction with the negatively charged phosphate groups of RNA. Therefore, this invention also relates to small organic molecules that are able to mimic this structural feature and thereby inhibit Rev/RRE interaction.

The method of inhibition described herein is useful in a variety of contexts. In an in vitro context the method of inhibition can be used, for example, as a positive control for Rev/RRE binding inhibition within an experiment designed to identify other compounds having this desirable property, as shown in the inhibition of replication of HIV.

The 2-DOS aminoglycoside can be functionalized and further tested for enhancement of the desired properties disclosed herein. The amine and hydroxy functionalities are preferred locations for derivatization. The functionalization of the 2-DOS aminoglycosides can serve to increase the affinity/specificity of the compounds for the RRE. The modifications can also serve to increase the membrane permeability and cellular uptake of the compounds. Derivitization with lipophilic moieties or groups that decrease basicity of the amines may have this desired effect. In a therapeutic context, the modified aminoglycosides may show decreased toxicity. Also, suitably modified 2-DOS aminoglycosides may not themselves be inhibitors of the Rev RRE interaction, but may be converted to the active inhibitors inside the cell.

In one embodiment, the amines of the 2-deoxystreptamine aminoglycoside with three attached Sugars are functionalized with modifying groups that increase the molecular weight of the 2-DOS aminoglycoside by no more than 500 daltons. In another embodiment, the amines of a 4,5-disubstituted 2-deoxystreptamine aminoglycoside are also functionalized with modifying groups that increase the molecular weight of the 2-DOS aminoglycoside by no more than 500 daltons. In a further embodiment, the amines of 2-deoxystreptamine aminoglycosides with one, two or three attached sugars, and of 4-monosubstituted and 4,6- disubstituted 2-deoxystrepamine aminoglycosides are functionalized with modifying groups with no molecular weight restriction. Common modifying groups include without limitation benzyl, substituted benzyl, N-tert-butoxycarbonyl, carbobenzyloxy, alkyl, substituted alkyl, acyl, benzoyl, substituted benzoyl, alkanoyl, or substituted alkanoyl. Preferably, the modifying group is one that tends to increase the overall lipophilicity of the 2-DOS aminoglycoside compounds.

In another embodiment, the amine modifying group is a methyl group provided that all amines in the 2-DOS aminoglycoside are either methyl substituted or primary amines. In this instance, the hydroxyl groups on the 2-DOS molecule may be non-substituted, partially substituted, or completely substituted.

The hydroxy functionalities of the 2-DOS aminoglycosides can also be functionalized with modifying groups. Common modifying groups which are useful for hydroxyl derivation include without limitation benzyl, substituted benzyl, benzoyl, substituted benzoyl, alkyl, substituted alkanoyl, substitued alkanoyl, or silyl. As discussed for amine derivitization, the hydroxyl modifying group is preferably one having a tendency to increase the overall lipophilicity of the 2-DOS aminoglycoside.

The following detailed structural information is presented in an effort to describe particularly useful 2-DOS aminoglycoside derivatives. These include 4-substituted, 4,5 disubstituted, or 4,6 disubstituted 2-deoxystreptamine aminoglycosides having the structural features set forth in Structure I below.

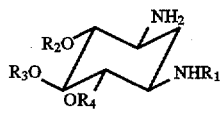

wherein $R_1$ is chosen from H or L-(−)-4-amino-2- hydroxybutyryl;

wherein $R_2$ is chosen from the group of hexoses having the structures according to Structure II:

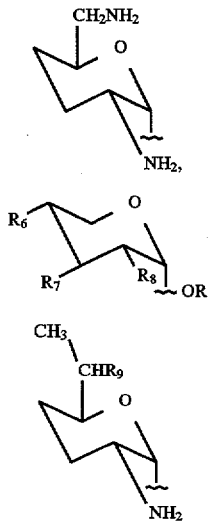

wherein $R_5$ can be either amino or hydroxyl;
wherein $R_6$ and $R_7$ can be either H or hydroxyl;
wherein $R_8$ can be either amino or hydroxyl;
wherein $R_9$ can be either amino or methylamino;

wherein $R_3$ and $R_4$ are independently selected from H, $R_{10}$, or moieties of the structures of Structure III:

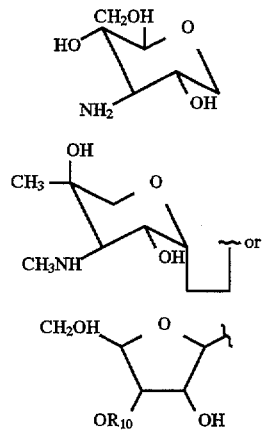

wherein $R_{10}$, as shown in Structure IV, is selected from the group consisting of H or

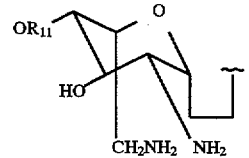

wherein $R_{11}$, is selected from the group consisting of H or mannosyl; but wherein at least one of $R_3$ or $R_4$ must be H.

It should be recognized that the amine and hydroxyl functionalities of the structures shown as Structures I-IV above can be modified as described above.

BIS-AMIDINE COMPOUNDS

Successful inhibition of binding of Rev to the high affinity RRE was observed with another class of small organic compounds, Bis-amidine compounds. These compounds have a general formula:

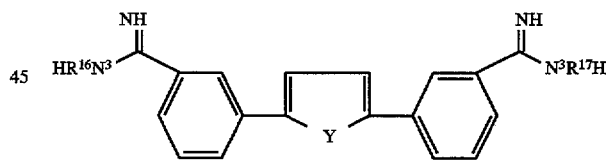

wherein Y is O or S;

$R^{16}$ and $R^{17}$ are independently selected from the group consisting of hydrogen, $C_2$ to $C_7$ alkyl, or a heterocyclic ring having 3–10 ring atoms; wherein the heterocyclic ring is optionally substituted with $C_1$–$C_6$ alkyl groups;

wherein the hetero atoms comprise N, and optionally O or S; and wherein, when $R^{16}$ and $R^{17}$, are alkyl groups, the alkyl groups are substituted with at least one of $C_1$ to $C_6$ dialkylamino, ($C_1$ to $C_6$ alkyl)(aryl)amino, di($C_1$–$C_6$ alkyl) amino($C_1$–$C_3$ alkyl)aryl, $C_3$–$C_8$ dicycloalkylamino, ($C_1$ to $C_6$ alkyl)($C_3$–$C_8$ cycloalkyl)amino, heterocyclic having 5 to about 7 ring atoms wherein the hetero atoms comprise N, and optionally O, or S.

Further, $R^{16}$, and $R^{17}$, can be optionally interrupted by oxygen, nitrogen, sulfur, or any combination thereof.

The subject invention also contemplates pharmaceutical compositions that incorporate an effective amount of the compounds having the formula as described hereinabove, and a pharmaceutically acceptable diluent or carrier.

The present invention includes a compound having the formula:

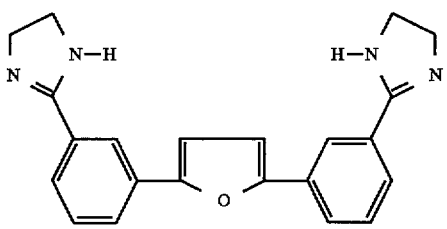

The compounds of the present invention having the formula:

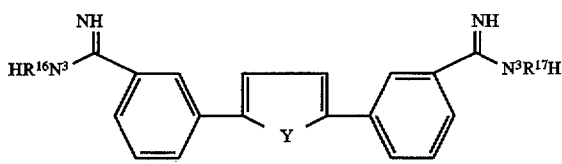

are readily synthesized following the sequence of reactions for the general synthesis as shown in FIG. 1. 3-Cyanoacetophenone, Compound 8, is brominated to produce α-bromo-3-cyanoacetophenone (Compound 10). An enamine (Compound 9) can be prepared from α-cyanoacetophenone and an amine (e.g., pyrrolidine). The enamine (9) is reacted with the α-bromo-3-cyanoacetophenone to provide a 1,4-diketone (Compound 11). The diketone is then cyclized by reaction with acetic anhydride to form the bis(cyanophenyl)-furan (Compound 12a). Alternatively, to prepare the thienyl (12b) compound, the diketone is (11) reacted with bis(dicyclohexyltin)sulfide and boron trichloride. The furanyl or thienyl compound is reacted with ethanolic hydrochloric acid (HCl) to produce the bis(ethyl imidate) dihydrochloride (Compound 14a or 14b). Finally, either Compound 14a or 14b is reacted with an amine to provide the furanyl and/or thienyl compounds of the present invention.

Non-limiting examples of groups which are useful for substitution on the $N^1$, $N^2$, or $N^3$, atoms in the preferred compounds are hydrogen, 3-N,N-dimethylaminopropyl, 3-N,N-diethylaminopropyl, 4-N,N-dimethylaminobutyl, 6-N,N-dimethylaminohexyl, 3-pyridylmethyl, 2-(1-methyl-2-pyrrolidinyl)ethyl, 2-pyrrolidinoethyl, 2-methylpiperidinopropyl, or an alkyl group having from about 3 to about 7 carbon atoms wherein said alkyl group is substituted with a dialkylamino group wherein said alkyl groups can each have from 1 to about 4 atoms.

A preferred compound when Y is oxygen is a compound wherein $R^{16}$ and $R^{17}$ are both 3-N,N-diethylaminopropyl. Preferred compounds when Y is sulfur are compounds wherein $R^{16}$ and $R^{17}$ are the same and are 3-N,N-diethylaminopropyl or 2-(1-methyl-2-pyrrolidinyl)ethyl.

APPLICATIONS

The present invention encompasses the inhibition of retroviral, and preferably HIV, replication in an infected cell, using as an inhibitory agent the 2,5-Bis(3-amidinophenyl) furan and 2,5-Bis(3-amidinophenyl)thiophene compounds disclosed herein, or analogues thereof. For treatment of HIV infection or disease in humans, the inhibitory compounds may be administered in any medically acceptable manner, e.g., via oral and enteral, intravenous, subcutaneous, intramuscular, intranasal, and transmucosal routes of administration.

HIV disease is defined herein as a number of HIV-related illnesses classified by the Center For Disease Control (CDC) (M.M.W.R. 35:334–339, 1987). These include acute primary infection syndromes, asymptomatic infection, persistent generalized lymphadenopathy, or symptomatic HIV infection. In general, any patient who is HIV virus-positive or with HIV antibody-positive status would be included.

The compounds may be formulated with physiologically acceptable carriers, e.g., water, physiological saline, and the like, and may be formulated in solutions, pills, creams, ointments, suppositories, or other useful forms. Additives known in the art may also be added, such as bacteriocidal agents, stabilizers, and the like. Typically, the concentration of the compounds of the present invention in a pharmaceutical formulation will range from about 1 to 90% (w/w), preferably about 10 to 50% (w/w).

It will be understood that effective amounts of the compounds need not be contained within a single dose of the above-described formulations, since administration of effective amounts may be achieved using a plurality of doses. An effective amount of these compounds corresponds to an amount that results in lessening or amelioration of the rate or degree of viral replication or other symptoms of infection. Such effective amounts will range from about 0.1 to 100 mg/kg body weight. Determination of the effective amounts of new compounds can be achieved using standard diagnostic evaluation methods that are well-known in the art.

The invention further contemplates the preparation of novel 1,4-diketones having the formula:

wherein $R^{22}$ and $R^{23}$ are aryl or heteroaryl. The aryl or herteroaryl groups can be substituted with substituents such as cyano, alkyl, alkoxy, alkoxycarbonyl, halo, nitro, and the like.

A preferred compound has the formula:

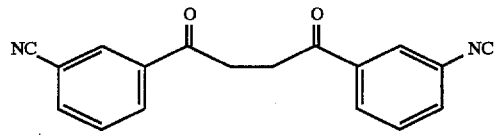

These butan-1,4-dione compounds can be prepared by reaction of the an enamine with an α-halomethylarylketones or α-halomethylheteroarylketones in an aprotic solvent such as dimethyl formamide (DMF), dimethylsulfoxide (DMSO), hexamethylphosphoramide (HMPA), N-methyl pyrrolidino, N,N-dimethylacetamide (DMAC) and the like. Typically, the reaction is carried out at about −78° C. Then the reaction the mixture is stirred at room temperature for about 20 hours and water added to hydrolyze the iminium salt. The 1,4-diketone is isolated by filtration.

Preparation of the Enamines:

Titanium (IV) chloride (20 mmol) in 20 mL dichloromethane is added to a vigorously stirred mixture of a 3-cyanoarylmethylketone or heteroarylmethylketone (40 mmol) and a secondary amine (120 mmol), such as, for example, pyrrolidine, morpholine, dimethylamine, and the like, in a nonreactive solvent, such as, for example, dichloromethane, tetrahydrofuran (THF), diethylether, and the like at a temperature of about −78 °C. The mixture is slowly warmed to room temperature and stirred for from about 0.5 to about 24 hours. The progress of enamine formation can be monitored by running $^1$H NMR on an aliquot of the reaction mixture.

Purification of enamines:

The enamines can be purified by addition of a nonpolar solvent such as, for example, pentane, hexane, heptane, and the like; to the reaction mixture in order to effect the precipitation of titanium dioxide and the amine HCL salt. The precipitates are removed from the enamine solution by centrifugation (or filtration). This process can be repeated in order to remove any amine HCl salt in the solution.

EXAMPLES

Example 1

Aminoglycoside Antibiotics that inhibit Rev Binding to the RRE of HIV RNA

To test whether antibiotics can block binding of Rev to the RRE, a 67-nt $^{32}$P-labeled RNA probe containing a high affinity Rev-binding site was incubated with purified E. coli derived Rev protein in the presence of various antibiotics. Binding of Rev to the RNA probe was quanitified by an RNA gel mobility shift assay.

A total of 32 aminoglycoside and nonaminoglycoside antibiotics were initially surveyed for their ability to inhibit Rev binding. Several conclusions follow from these data. First, no nonaminoglycoside antibiotic tested (i.e., erythromycin, tetracycline, thiostreption, chloramphenicol, chromomycin A, olivomycin, lincomycin, clindamycin A, vineomycin, capreomycin, viomycin, distamycin A, ampicilin, carbenicilin and tunicamycin) was inhibitory at any concentration tested. Second, three of the aminoglycoside antibiotics (i.e., neomycin B, tobramycin, and lividomycin A) had significant inhibitory ability. In particular, neomycin B completely inhibited Rev binding at concentrations as low as 1 µM. This same concentration of drug also inhibited binding of Rev to (i) a 33-nt RNA probe that contained a high affinity binding site and (ii) a 234-nt RRE that supports a Rev response in vivo. Tobramycin and lividomycin A both require a slightly higher concentration (10 µM) to achieve inhibition of Rev binding. The third group of aminoglycosides was inhibitory at 100 µm (i.e., gentramicin, kanamycin B, ribostamycin, neamine, amikacin and sisomycin). The remaining aminoglycoside antibiotics tested had no inhibitory activity at any concentration tested (i.e., butirosin, kanamycin A, paromomycin, specitinomycin, and stretomycin, kasugamycin, dihydrostreptomycin and hygromyoin B).

Association of aminoglycosides with RNA may involve ionic interactions between the positively charged amino groups of the drugs and negatively charged phosphate groups of RNA. The importance of the amino groups for RNA binding is revealed by several important structure-activity relationships: in the cases of both (i) kanamycin A versus kanamycin B, and (ii) neomycin B versus paromomycin, changing a single amino to a hydroxyl group completely eliminated inhibitory activity.

The Rev-RRE inhibition data suggest that a 2-deoxystreptamine (2-DOS) core structure promoted inhibition of REV-RRE interaction. For example, drugs lacking 2-DOS, such as streptomycin and spectinoymycin, were inactive in this assay, as were nonaminoglycoside antibiotics. The most active aminoglycosides contain a 4,5-disubstituted 2-DOS (neomycin B and lividomycin A) or a 4,6-disubstituted 2-DOS (tobramycin).

The most striking structure-activity relationship is illustrated in the comparison between neomycin B and paromomycin. These two molecules are almost identical, differing only in the nature of the $C_6$ substituent of the aminoglucose at the 4 position of 2-DOS. Neomycin B, the most potent inhibitor, has an amino group, whereas paromomycin, which is completely inactive, has a hydroxyl group at the position.

Example 2

Lack of Effect Neomycin B on Non- Rev RRE interactions

To determine whether inhibition by 2-DOS aminoglycosides was specific for Rev-RRE interaction, the effect of inhibitory antibiotics on several unrelated sequence-specific RNA- and DNA-binding proteins was examined. Initially, two well-characterized proteins involved in pre-mRNA splicing were examined: the essential splicing factor USAF[65] and the Drosophila splicing regulator Sex lethal.

In these binding experiments, Sex lethal protein or the 65 kD subunit of U2AF[65], each purified as fusion protein with gluthatione-S-transferase (GST), were incubated with a $^{32}$P-labelled RNA containing the well-characterized polypyrimidine tract-3' splice site found in the Drosophila tra gene. The incubations were performed in the absence or presence of 100 µM neomycin B or 100 µM tobramycin.

The binding of GST-Sex lethal to the tra RNA is unaffected after incubation with 100 µM neomycin B. Similarly, in vitro binding properties of these two RNA binding proteins unrelated to Rev.

Glyceraldehyde 3-phosphate dehydrogenase (GAPDH), a glycolytic enzyme that binds to a subset to transfer RNAs (tRNAs) in a sequence-specific manner, was also analyzed for its sensitivity to 2-DOS antibiotics. The binding of GAPDH to tRNA$^{Tyr}$ was unaffected by 100 µM neomycin B or 100 µM tobramycin.

Rev is a member of a class of RNA-binding proteins containing an arginine-rich RNA-binding motif. Whether aminoglycoside antibiotics could inhibit binding of another member of this class, the HIV-1 Tat protein, was examined next. A 12 amino acid peptide containing the Tat arginine-rich region possesses an RNA binding activity comparable to that of the full-length protein. Binding of the Tat peptide to its cognate sequence was not affected by any of the aminoglycoside antibiotics. Thus, of all the RNA-protein interactions tested, only the Rev-RRE interaction was inhibited.

Example 3

Lack of effect of Neomycin B on DNA Binding Proteins

In the following experiments, the effect of neomycin B on the in vitro binding properties of DNA binding proteins was examined.

In these studies, the DNA binding activities of two eukaryotic transcription factors, Oct-1 and ATF-2, were analyzed using a gel mobility shift assay. Purified Oct-1 was inculcated in the absence or presence of 100 µM neomycin B with a $^{32}$P-labelled 70-nt DNA probe containing an HSV ICPO octamer binding site (Stern and Her, Genes and Development, 5:2555–2566 (1991)). Additionally, the effect of 100 µM neomycin B on the binding of ATF-2 to a 35-nt DNA probe homologous to nucleotides −251 to −232 of the HTLV-1 LTR was analyzed. The binding of Oct-1 to the HSV ICPO octamer binding site was unaffected by 100 µM neomycin B. The level of DNA binding activity of ATF-2 to the HTLV-1 LTR also remained unchanged after incubation with 100 µM neomycin B. Thus, neomycin B has no affect on the in vitro DNA binding properties of either Oct-1 or ATF-2.

Example 4

Inhibition of Precursor mRNA Processing

Previous studies have reported that aminoglycoside antibiotics such as neomycin B and tobramycin effectively inhibit self-splicing of Group I introns in vitro (von Ahsen et al., *J. Mol. Biol.*, 226:935–941 (1992). To determine whether these aminoglycoside antibiotics also inhibit precursor mRNA splicing, the effect of kanamycin A, neomycin B or tobramycin on mRNA processing was tested in an in vitro system. In these studies, a 220-nt adenovirus major late precursor mRNA (MXSVL) was incubated in HeLa cell nuclear extracts in the presence or absence of kanamycin A, neomycin B, or tobramycin. The addition of these aminoglycoside antibiotics at concentrations up to 100 µM to in vitro mammalian splicing extracts had no effect on either step of precursor mRNA splicing. These data support the conclusion that the inhibition of Rev binding to the RRE by neomycin is highly specific to this particular RNA protein interaction.

Example 5

Neomycin B Binds to the Core Binding Site of RRE

The experiments described below were performed to determine whether or not neomycin B complexes directly with the RRE and thus blocks Rev binding. To this end, chemical footprinting experiments were performed. The 67-nt RRE RNA was incubated alone, with Rev, or with increasing concentrations of neomycin B, tobramycin, or kanamycin A, (0.1, 1.0 and 10 µM). The incubation mixtures were then treated with either dimethyl sulfate (DMS), which methylates adenosine at N1 and cytosine at N3, or with kethoxal, which modifies N1 and N2 of guanosine. Modification of specific bases was detected by primer extension. Under these conditions, DMS and kethoxal are single strand-specific, and thus the modification pattern of RNA alone provides an indication of secondary structure.

The results of these experiments demonstrated that neomycin B binds to nucleotides within the RRE, specifically those contained within the high affinity recognition/binding site for the Rev protein. Tobramycin produced similar protection patterns, although protection by tobramycin was weaker, a result that is consistent with its weaker inhibitory activity. For example, Rev, neomycin B, and tobramycin all strongly protected residues 46–48 of the 67-nt RNA. Similar concentrations of the non-inhibiting aminoglycoside kanamycin A did not protect the RRE from chemical modification.

Example 6

Rev Competes with Neomycin B for Binding to the RRE

The chemical modification/protection experiments described in Example 5 revealed that the inhibitory 2-DOS antibiotics protected bases within the core of the high affinity Rev-binding site. This suggested that the drugs inhibited Rev binding by a competitive mechanism. A prediction of this hypothesis is that inhibition could be overcome by high concentrations of Rev. To test this possibility, increasing amounts of Rev were added to a reaction mixture containing 100 µM neomycin B. At the lowest protein amounts (1.3–2 ng), Rev binding was completely inhibited by the drug. However, as the amount of Rev was increased (i.e., to 10–20 ng), RNA binding was restored. The combined results of the experiments described in Examples 5 and 6 indicate that inhibition by neomycin B of Rev binding to the RRE occurs by a competitive mechanism.

Example 7

Neomycin B antagonizes Rev Function In Vitro

The experiments described above measured the ability of 2-DOS antibiotics to interfere with binding of purified Rev to RNA. This suggested that inhibitory antibiotics could also interfere with Rev function. This hypothesis was tested by analyzing Rev function in vitro. In this assay, inhibition of splicing requires both a Rev derivative that can bind RNA, as well as a pre-mRNA containing the RRE. Thus, splicing repression is dependent upon the Rev-RRE interaction. Because neomycin B inhibited Rev binding, it was believed that the drug would reverse splicing repression.

The results of this experiment showed that the Rev derivative inhibited splicing of the RRE-containing pre-mRNA. Significantly, neomycin B counteracted the Rev-mediated repression of splicing, at concentrations similar to those that inhibited Rev binding (1.0–2.5µM). In contrast, a 40-fold higher concentration of the noninhibitory antibiotic kanamycin A failed to reverse splicing repression. This demonstrates that neomycin B inhibits Rev function in vitro. Because a 400-fold higher concentration of neomycin B did not inhibit the RNA-based pre-mRNA splicing reaction (See Example 4) it is evident that inhibition is highly specific.

Example 8

Neomycin B Selectively Antagonizes Rev Function In Vivo

The experiments described below were performed to determine whether or not the inhibitory 2-DOS antibiotics antagonize Rev function in vivo. Rev function was measured in a cotransfection assay using the chloramphenicol acetytransferase (CAT) reporter plasmid pCM128, which has a single intron containing both the RRE and the bacterial CAT coding sequence (Hope et al., Proc. Natl. Acad. Sci. USA, 87:7787–7791 (1990)). Normally, the intron is efficiently excised by splicing; therefore, cells transfected with pCM128 express only trace amounts of CAT enzyme activity. Cotransfection with a Rev expression plasmid permits unspliced transcripts to enter the cytoplasm, and thus CAT expression is increased. In this assay, inclusion of either neomycin B or tobramycin resulted in a dose-dependent inhibition of Rev function, whereas kanamycin A had no effect. These findings parallel the results obtained in the in vitro Rev binding and splicing inhibition assays described above.

Three considerations indicated that the inhibition of Rev function was specific, and was not due to a more general inhibitory effect on gene expression. First, at all concentrations of antibiotics tested, cellular viability and growth were normal, and total cellular protein synthesis (as monitored by incorporation of [$^{35}$S]methionine into protein) was not inhibited. Second, concentrations of neomycin B and tobramycin that inhibited Rev function did not inhibit expression of a cotransfected β-galactosidase reporter gene. Third, comparable concentrations of neomycin B and tobramycin did not inhibit either expression of a cytomegalovirus (CMV)-CAT reporter, or HIV Tat-mediated activation of an HIV LTR-CAT reporter gene. Thus, inhibition of Rev function is not due to interference with CAT gene expression at the transcriptional or posttranscriptional level. The failure to inhibit Tat is particularly relevant, because transcription activation involves an RNA-protein interaction between Tat and trans-acting responsive sequences. These data indicate that neomycin B and tobramycin selectively inhibit Rev function in vivo.

Example 9

Neomycin B Inhibits Production of HIV

The experiment described below was performed to test whether or not neomycin B inhibits production of HIV in an infected cell. A chronically HIV-infected cell line, U1, was used. This cell line has been previously used as a model to study Rev-dependent activation of viral production. (Pomerantz, et al., *Cell*, 61:1271–1276 (1990); Michael, et al., *J. Virol.*, 55:1291–1303, (1991)).

Viral production was assessed after exposure of cells to increasing concentrations of neomycin B, using a standard assay that quantifies the amount of an HIV structure protein, p24, in the culture medium. Neomycin B strongly inhibited viral production in a dose-dependent fashion (0–2.5 mM); at the highest concentration of necomycin tested, inhibition of viral production was approximately 85%. Significantly, at all concentrations of neomycin, cellular growth was 94%–108% of the untreated control. Neomycin B thus clearly inhibits production of HIV in chronically infected cells.

Example 10

Synthesis of α-Bromo-3-cyanoacetophenone (Compound 10)

A solution of bromine (0.92 mL, 17.9 mmol) in 8 mL dichloromethane was added to 3-cyanoacetophenone (2.60 g, 17.9 mmol) in 11 mL dichloromethane over 10 min at 5°–10° C. The mixture was warmed to room temperature and stirred for 1 hour. Water (25 mL) was added to the mixture. The organic layer was separated, dried over $Na_2SO_4$, and concentrated to a yellow solid (3–50 g). The yellow solid was recrystallized from 95% EtOH to afford compound 10 as white crystals. Yield: 2.22 g (55%).

The properties of α-bromo-3-cyanoacetophenone are listed below:

$^1$H NMR ($CDCl_3$, 300 MHz) δ 8.08 (m,2H), 7.81 (m, 2H), 4.43 (s, 2H).

$^{13}$C NMR ($CDCl_3$, 75 MHz, APT) δ 189.58 (C), 136.77 (CH), 134.71 (C), 132.66 (CH), 130.02 (CH), 117.69 (C), 113.53 (C), 30.07 ($CH_2$).

Example 11

Synthesis of 1,4-Bis(3-cyanophenyl)butan-1,4-dione (Compound 11)

(1) Titanium (IV) chloride (2.20 mL, 3.80 g, 20.0 mmol) in 20 mL dichloromethane was added to a vigorously stirred mixture of 3-cyanoacetophone (8) (5.81 g, 40.0 mmol) and pyrrolidine, 10.0 mL, 8.53 g, 120 mmol) in 120 mL dichloromethane over 20 min at −78° C. The mixture was slowly warmed to room temperature and stirred for 6 hours. A precipitate formed and the mixture turned to an orange color. Pentane (50 mL) was added and the mixture was centrifuged to remove the white precipitate. Removal of the solvents from the supernatant provided an orange oil. The orange residue was treated with 100 mL pentane and centrifuged. After removing solvents from the supernatant. The enamine (9) was obtained as a yellow solid. Yield: 2.91 g (37%).

The properties of the enamine are listed below:

$^1$H NMR ($CDCl_3$, 300 MHz) δ 7.70 (m,1H), 7.60 (m, 2H), .7.42 (m, 1H), 3.91 (Apparent doublet, j=5.18 Hz, 2H)

(2) The enamine (9) (2.91 g, 14.7 mmol) was dissolved in 40 mL DMF. The solution was cooled to −78° C. and 2-Bromo- 3'-cyanoacetophone (10) (3.45 g, 15.4 mmol) in 20 mL DMF was added over 5 min. The reaction mixture was warmed to 22° C. and stirred overnight. Water (100 mL) was added to the mixture, and a yellow precipitate formed. The mixture was stirred for an additional 3 hours. The mixture was filtered, the yellow precipitate washed with MeOH (4×4 mL) and dried to afford the 1,4-diketone (11) 2.34 g (55 %).

The properties of the 1,4-Bis(3-cyanophenyl) butan-1,4-dione are listed below: M.P. 190° C.;

$^1$H NMR ($CDCl_3$, 300 MHz) δ 8.32 (m, 2H), 8.25 (m, 2H), 7.88 (m, 2H), 7.65 (m, 2H), 3.48 (s, 4H).

$^{13}$C NMR ($CDCl_3$, 75 MHz, APT) δ 196.31 (C), 137.29 (C), 136.26 (CH), 132.11 (CH), 131.91 (CH), 129.82 (CH), 117.93 (C), 113.34 (C), 32.54 ($CH_2$).

EI MS m/e: 288 ($M^+$, 10%)

Example 12

Synthesis of 2,5-Bis(3-cyanophenyl) furan (Compound 12a)

A mixture of diketone 11 (301 mg, 1.04 mmol), acetic anhydride (10 mL), and concentrated $H_2SO_4$ (2 drops) was heated at reflux for 10 min. The mixture was poured into 30 mL crushed ice. The light brown precipitate was filtered and dried (yield: 320 mg). The crude product was dissolved in 2 mL $CHCl_3$ and chromatographed on a silica column (2×20 cm), eluted with $CHCl_3$. Fractions ($R_f$=0.75, 10% EtOAc/$CHCl_3$) were combined and concentrated to give the title compound (160 mg, 57%)

The properties of the 2,5-Bis(3-cyanophenyl)furan are listed below: M.P. 163°–164° C.;

$^1$H NMR ($CDCl_3$, 300 MHz) δ 8.02 (m, 2H), 7.88 (m, 2H), 7.57 (m, 4H), 6.88 (s, 2H).

$^{13}$C NMR ($CDCl_3$, 75 MHz, APT) δ 152.02 (C), 131.33 (C), 130.93 (CH), 129.77 (CH), 127.75(CH), 127.26 (CH), 118.50 (C), 113.28 (C), 109.28 (CH).

EI MS m/e: 270 ($M^+$, 65%)

Example 13

Synthesis of 2,5-Bis(3-cyanophenyl)thiophene (Compound 12b)

To a mixture of diketone 11 (288 mg, 1.00 mmol) and bis(tricyclohexyltin) sulfide (1.537 g, 2.00 mmol) in 15 mL toluene was added a 1 M solution of boron trichloride (1.3 mL, 1.3 mmol) in xylenes. The mixture was heated at reflux for 1.5 hours. Hexane (15 mL) was added to the mixture and the mixture was filtered. The crude thiophene (260 mg) was purified on a silica column (2×20 cm, $CHCl_3$, $R_f$=0.84 in 10% EtOAc/$CHCl_3$) to afford pure thiophene (180 mg, 63%) as a white solid.

The properties of the 2, 5-Bis(3-cyanophenyl)thiophene are listed below: M.P. 183.3°–184.2° C.;

$^1$H NMR ($CDCl_3$, 300 MHz) δ 7.90 (m, 2H), 7.84 (m, 2H), 7.59 (m, 2H), 7.52 (m, 2H), 7.37 (s, 2H).

$^{13}$C NMR ($CDCl_3$, 75 MHz, APT) δ 142.29 (C), 135.10 (C), 131.09 (CH), 129.96 (CH), 129.81 (CH), 129.03 (CH), 125.64 (CH), 118.41 (C), 113.44 (C).

EI MS m/e: 286 ($M^+$, 100%)

Example 14

General Procedure for the Synthesis of Bisamidines (Compounds 15–25)

(1) HCl gas was bubbled through a suspension of the appropriate bis(3-cyanophenyl)furan(12a) [or thiophene (12b)](19 to 60 mg) in about 2 mL EtOH for 3 min at 0° C. The resulting mixture was sealed and stirred at room temperature for 2 days. Solvent was removed in vacuo to provide the corresponding imidate HCl salt (Compounds 14a or 14b).

The properties of the 2,5-Bis(3-imidocarboethoxyphenyl) furan (Compound 14a; Y=O) are listed below:

$^1$H NMR (CD$_3$OD, 300 MHz), δ 8.48 (m, 2H), 8.26 (m, 2H), 7.96 (m, 2H), 7.74 (t,J=7.9 Hz, 2H), 7.17 (s, 2H), 4.68 (q,J=7.0 Hz, 4H), 1.66 (t,J=7.0 Hz, 6H);

The properties of the 2, 5-Bis(3-imidocarboethoxyphenyl) thiophene (Compound 14b; Y=S) are listed below:

$^1$H NMR (CD$_3$OD, 300 MHz) 38.42 (m, 2H), 8.11 (m, 2H), 7.96 (m, 2H), 7.82 (s, 2H), 7.72 (t,J=7.7 Hz, 2H), 4.61 (q,J=6.9 Hz, 4H), 1.51 (t,J=7.0 Hz, 6H).

(2) The yellow imidate HCl salt was dissolved in appropriate amount of EtOH to form the imidate stock solution. Portions of this stock solution were taken to react with an amine or amines (2 equivalents) in the presence of triethylamine (2–6 equivalents) for 2–4 days. The resulting amidine(s) were precipitated out by the addition of EtOAc (45 mL). The mixture was centrifuged and decanted to provide the pure amidine(s) as a white or yellow solid.

Example 15

Synthesis of 2,5-Bis [3-(3-N,N-dimethylaminopropylamidino) phenyl]furan (Compound 15)

Following the method of Example 14, step 2, imidate (14a) (10.3 μmol) in 1 mL EtOH was treated with 3-N,N-dimethyl-propylamine (2.60 uL, 20.6 μmol). The title compound was obtained as a yellow solid in 77% yield (4.3 mg).

The properties of the amidinophenylfuran are listed below:

$^1$H NMR (CD$_3$OD, 300 MHz) 38.19 (m, 4H), 7.70 (m, 4H), 7.13 (s, 2H), 3.55 (m,4H), 2.52 (m, 4H), 2.35 (s, 12H), 198 (m, 4H).

FAB MS m/e: 476 (M+, 100%) (sample was prepared in CD$_3$OD).

Example 16

Synthesis of 2,5-Bis[3-N,N-diethylaminopropylamidino phenyl]furan (Compound 16)

Following the method of Example 14, step 2, imidate (14a) ( 10.3 μmol) in 1 mL EtOH was treated with 3-N,N-diethylaminopropylamine (3.2 μL, 20.6 μmol). The title compound was obtained as a yellow solid in 58% yield (3.5 mg).

The properties of the amidinophenylfuran are listed below:

$^1$H NMR (CD$_3$OD, 300 MHz) 38.18 (m, 4H), 7.67 (m, 4H), 7.15 (s, 2H), 3.57 (m, 4H), 2.75 (s, 12H), 2.00 (m, 4H), 1.10 (t, 12H).

Example 17

Synthesis of 2,5-Bis[3-(4-N,N-dimethylaminobutyl-amidino)phenyl]furan (Compound 17)

Following the method of Example 14, step 2, imidate (14a) (9.25 μmol) in 1 mL EtOH was treated with 4-N,N-dimethylaminobutylamine (2.50 uL, 18.5 μmol). The title compound was obtained as a yellow solid in 43% yield (2.3 mg).

The properties of the amidinophenylfuran are listed below:

$^1$H NMR (CD$_3$OD, 300 MHz) 38.19 (m, 4H), 7.68 (m, 4H), 7.17 (s, 2H), 3.53 (t,J=6.6 Hz, 4H), 2.82 (m, 4H), 2.58 (s, 12H), 1.82 (m, 8H).

Example 18

Synthesis of 2,5-Bis[3-(6-N,N-dimethylaminohexylamidino)phenyl]furan (Compound 18)

Following the method of Example 14, step 2, imidate (14a) (9.25 μmol) in 1 mL EtOH was treated with 6-N,N-dimethyl- aminohexylamine (3.04 uL, 18.5 μmol). The title compound was obtained as a yellow solid in 79% yield (4.6 mg).

The properties of the amidinophenylfuran are listed below:

$^1$H NMR (CD$_3$OD, 300 MHz) 58.18 (m, 4H), 7.67 (m, 4H), 7.16 (s, 2H), 3.50 (t,J=7.4 Hz, 4H), 2.82 (t,J=7.8 Hz, 4H), 2.62 (s, 12H), 1.82 (m, 4H), 1.69 (m, 4H), 1.50 (m, 8H).

Example 19

Synthesis of 2,5-Bis(3-imidazolinophenyl)furan (Compound 19)

Following the method of Example 14, step 2, imidate (14a) (8.1/μmol) in 1 mL EtOH was treated with 1,2-ethylenediamine (1.10 uL, 16.2/μmol). The title compound was obtained as a white solid in 100% yield (3.6 mg).

The properties of the amidinophenylfuran are listed below:

$^1$H NMR (CD$_3$OD, 300 MHz) 58.37 (m, 2H), 8.12 (m, 2H), 7.75 (m, 2H), 7.64 (m, 2H), 7.09 (s, 2H), 4.01 (s, 8H).

Example 20

Synthesis of 2,5-Bis[3-pyridylmethylamidinophenyl] thiophene (Compound 20)

Following the method of Example 14, step 2, imidate (14b) (11.6 μmol) in 1 mL EtOH was treated with 3-(aminomethyl) pyridine (2.40 uL, 23.3 μmol). The title compound was obtained as a yellow solid in 78% yield (5.2 mg).

The properties of the amidinophenylthiophene are listed below:

$^1$H NMR (CD$_3$OD, 300 MHz) δ 8.70 (br s, 2H), 8.58 (br s, 2H), 8.12 (m, 2H), 8.00 (m,2H), 7.70 (m,6H), 7.62 (s, 2H), 7.53 (br s,2H), 4.78 (s,4H)

Example 21

Synthesis of 2,5-Bis{3-[2-(1-methyl-2-pyrrolidinyl) ethylamidino]phenyl}thiophene (Compound 21 )

Following the method of Example 14, step 2, imidate (14b) (11.6 μmol) in 1 mL EtOH was treated with 2-(2-aminoethyl)-1-methylpyrrolidine (3.40 uL, 23.3 μmol). The title compound was obtained as a yellow solid in 86% yield (6.1 mg).

The properties of the amidinophenylthiophene are listed below:

$^1$H NMR (CD$_3$OD, 300 MHz) δ 8.05 (m,4H), 7.68 (m,4H), 7.64 (s, 2H), 3.55 (m,4H), 3.17 (m, 2H), 2.46 (s,6H), 2.43 (m,4H), 2.18 (m, 4H), 1.87 (m,6H), 1.66 (m,2H).

Example 22

Synthesis 2,5-Bis-[3-(3-N,N-diethylaminopropyl-amidino) phenyl]thiophene (Compound 22)

Following the method of Example 14, step 2, imidate (1 4b) (11.6 μmol) in 1 mL EtOH was treated with 3-N,N- diethylaminopropylamine (3.60 uL, 23.3 μmol). The title compound was obtained as a yellow solid in 64% yield mg).

The properties of the amidinophenylthiophene are listed below:

$^1$H NMR (CD$_3$OD, 300 MHz) δ 8.05 (m, 4H), 7.68 (m, 4H), 7.64 (s, 2H), 3.56 (m, 4H), 2.73 (m, 12H), 2.10 (m, 4H, 1.11 (t,J=7.1 Hz, 12H).

Example 23

Synthesis of 2,5-Bis[3-(2-pyrrolidinoethylamidino)phenyl] thiophene (Compound 23)

Following the method of Example 14, step 2, imidate (14b) (11.6 μmol) in 1 mL EtOH was with 1-(2-aminoethyl) pyrrolidine (2–90 uL, 23.3 μmol). The title compound was obtained as a yellow solid in 100% yield (6.8 mg).

The properties of the amidinophenylthiophene are listed below:

$^1$H NMR (CD$_3$OD,300 MHz) a 8.13 (m, 2H), 8.03 (m, 2H), 7.68 (m, 4H), 7.64 (s, 2H), 3.67 (t,J=5.9 Hz,4H), 2.96 (t,J=6.0 Hz, 4H), 2.75 (m, 8H), 1.90 (m, 8H).

Example 24

Synthesis of 2,5-Bis[3-(4-morpholinoamidino) phenyl] thiophene (Compound 24)

Following the method of Example 14, step 2, imidate (14b) (11.6 μmol) in 1 mL EtOH was treated with 4-aminomorpholine (2.30 uL, 23.3 μmol). The title compound was obtained as a yellow solid in 63% yield (4.1 mg).

The properties of the amidinophenylthiophene are listed below:

$^1$H NMR (CD$_3$OD,300 MHz) a 8.14 (m, 2H), 7.80 (m, 4H), 7.50 (m, 4H), 3.80 (m, 8H), 3.15 (m, 8H).

Example 25

Synthesis of 2,5-Bis{3-[3-(2-methylpiperidino)-propylamidino]phenyl}thiophene (Compound 25)

Following the method of Example 14, step 2, imidate (14b) (11.6 μmol) in 1 mL EtOH was treated with 1-(3-aminopropyl)-2-methylpiperidine (4.10 uL, 23.3 μmol). The title compound was obtained as a yellow solid in 80% yield (6.2 mg).

The properties of the amidinophenylthiophene are listed below:

$^1$H NMR (CD$_3$OD,300 MHz) δ 8.08 (m, 4H), 7.69 (m, 4H), 7.63 (s, 2H), 3.65 (m, 4H), 2.52 (m, 4H), 2.30 (m, 2H), 2.00 (m, 4H), 1.68 (m, 8H), 1.35 (m, 4H), 1.15 (d,J=6.3 Hz, 6H).

Example 26

Synthesis of 2,5-Bis[(3-amidino)phenyl]thiophenes derived from imidate 14b and a mixture of three amines.

Following the method of Example 14, step 2, imidate (14b) (6.67 μmol) in 1 mL EtOH was treated with 6.7 uL(13.4 μmol) of a EtOH solution (2 mmol/mL) containing an equimolar mixture of three amines, 3-aminomethyl) pyridine, 2-(2-aminoethyl)-I-methylpyrrolidine, and 3-N,N-diethylaminopropylamine. The title amidines (assuming 100% yield) were dissolved in 1 mL DMSO and used directly for biological assays.

Example 27

Synthesis of 2,5-Bis[(3-amidino)phenyl]thiophenes derived from imidate 14b and a mixture of three amines Following the method of Example 14, step 2, imidate (14b) (6.67 μmol) in 1 mL EtOH was treated with 6.7 uL(13.4 μmol) of a EtOH solution (2 mmol/mL) containing an equimolar mixture of three amines, 1-(2-aminoethyl) pyrrolidine, 4-aminomorpholine, and 1-(3-aminopropyl)-2-methylpiperidine. The title amidines (assuming 100% yield) were dissolved in 1 mL DMSO and used directly for biological assays.

Example 28

Synthesis of 2,5-Bis[(3-amidino) phenyl]thiophenes derived from imidate 14b and a mixture of two amines.

Following the method of Example 14, step 2, imidate (14b) (11.6 μmol) in 1 mL EtOH was treated with 11.6 uL (23.2 μmol) of a ETOH solution (2 mmol/mL) containing an equimolar mixture of two amines, 3-(aminomethyl)pyridine and 2-(2-aminoethyl)-I-methylpyrrolidine. The title amidines (assuming 100% yield) were dissolved in 3.85 mL DMSO and used directly for biological assays.

Example 29

Synthesis of 2,5-Bis[(3-amidino)phenyl]thiophenes derived from imidate, 14b and a mixture of two amines.

Following the method of Example 14, step 2, imidate (14b) (11.6 μmol) in 1 mL EtOH was treated with 11.6 uL(23.2 μmol) of a EtOH solution (2 mmol/mL) containing an equimolar mixture of two amines, 3-(aminomethyl) pyridine and 3-N,N-diethylaminopropylamine. The title amidines (assuming 100% yield) were dissolved in 3.85 mL DMSO and used directly for biological assays.

Example 30

Synthesis of 2,5-Bis[3-amidino)phenyl]thiophenes derived from imidate 14b and a mixture of two amines.

Following the method of Example 14, step 2, imidate (14b) (11.6 μmol) in 1 mL EtOH was treated with 11.6 uL(23.2 μmol) of a EtOH solution (2 mmol/mL) containing an equimolar mixture of two amines, 2-(2-aminoethyl)-1-methylpyrrolidine and 3-N,N-diethylaminopropylamine. The title amidines (assuming 100% yield) were dissolved in 3.85 mL DMSO and used directly for biological assays.

Example 31

Synthesis of 2,5-Bis[(3-amidino)phenyl]thiophenes derived from imidate 14b and a mixture of two amines Following the method of Example 14, step 2, imidate (14b) (11.6 μmol) in 1 mL EtOH was treated with 11.6 uL(23.2 μmol) of a EtOH solution (2 mmol/mL) containing an equimolar mixture of two amines, 1-(2-aminoethyl) pyrrolidine and 4-aminomorpholine. The title amidines (assuming 100% yield) were dissolved in 3.85 mL DMSO and used directly for biological assays.

Example 32

Synthesis of 2,5-Bis[(3-amidino)phenyl]thiophenes derived from imidate 14b and a mixture of two amines.

Following the method of Example 14, step 2, imidate (14b) (11.6 μmol) in 1 mL EtOH was treated with 11.6 uL(23.2 μmol) of a EtOH solution (2 mmol/mL) containing an equimolar mixture of two amines, 1-(2-aminoethyl) pyrrolidine and 1-(3-aminopropyl)-2-methylpiperidine. The title amidines (assuming 100% yield) were dissolved in 3.85 mL DMSO and used directly for biological assays.

Example 33

Synthesis of 2,5-Bis[(3-amidino)phenyl]thiophenes derived from imidate 14b and a mixture of two amines.

Following the method of Example 14, step 2, imidate (14b) (11.6 μmol) in 1 mL EtOH was treated with 11.6 uL(23.2 μmol) of a EtOH solution (2 mmol/mL) containing an equimolar mixture of two amines, 4-aminomorpholine and 1-(3-aminopropyl)-2-methylpiperidine. The title amidines (assuming 100% yield) were dissolved in 3.85 mL DMSO and used directly for biological assays.

Example 34

Inhibition of Binding of Rev to RRE by 2,5-Bis[3-(3-N,N-dimethylaminopropylamidino)Phenyl]furan The following experiment was performed to test whether 2,5-Bis[3-(3-N,N-dimethylaminopropylamidino)phenyl] furan (Compound 15, prepared as described in Example 15) inhibits the binding of HIV Rev protein to the HIV RRE.

A 69-nt $^{32}$P-labelled RNA probe containing a high affinity Rev-binding site (Bartel et al., *Cell* 67:529, 1991 ) was incubated with purified *E. coli*-derived Rev protein in the absence and presence of increasing concentrations of Compound 15. Reactions conditions were those that maximize the specificity of the interaction between Rev and the RRE, i.e., 150 mM KCl and a 100-fold molar excess of tRNA.

After a 30-minute incubation at room temperature, a nitrocellulose filter-binding assay was performed to quantify the binding of Rev to the RRE (Daly et al., *Biochem.* 32:10497, 1993). In this assay, RNA is retained on the filter only by virtue of binding to Rev. Filter-associated radioactivity was quantified in a Wallac Microbeta counter. The fraction of input RNA retained on the filter was plotted as a function of Compound 15 concentration, and the IC$_{50}$ (the concentration required to inhibit 50% Rev-RRE binding) was determined by linear regression.

Figure 2:
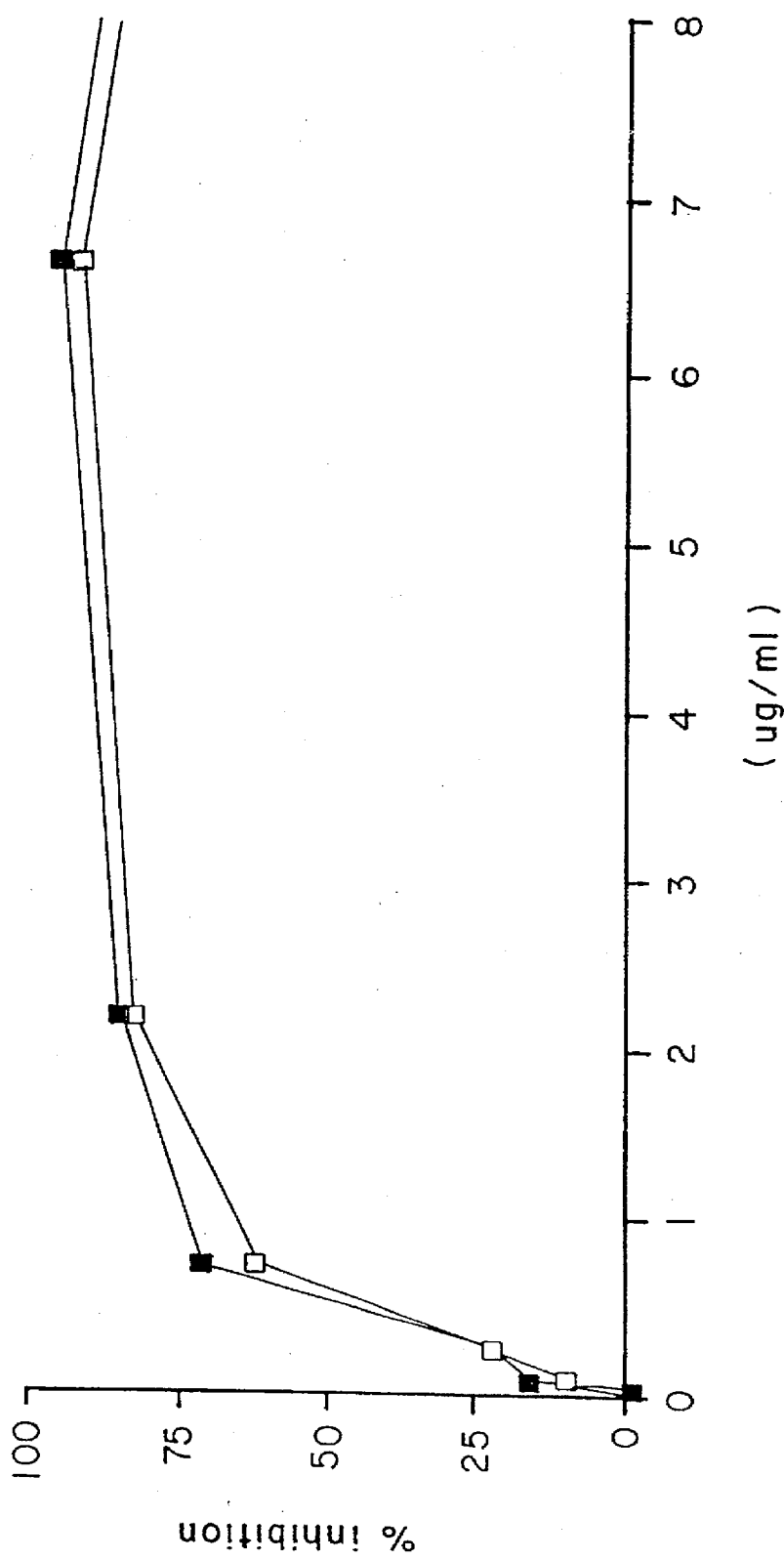
FIG. 2 is a graph showing the effect of increasing concentrations of 2,5-Bis[3-(3-N,N-dimethylaminopropylamidino)phenyl]furan on the binding of HIV Rev protein to an RNA containing the high affinity binding site (Domain II) of the Rev-responsive element (RRE).
Figure 3:
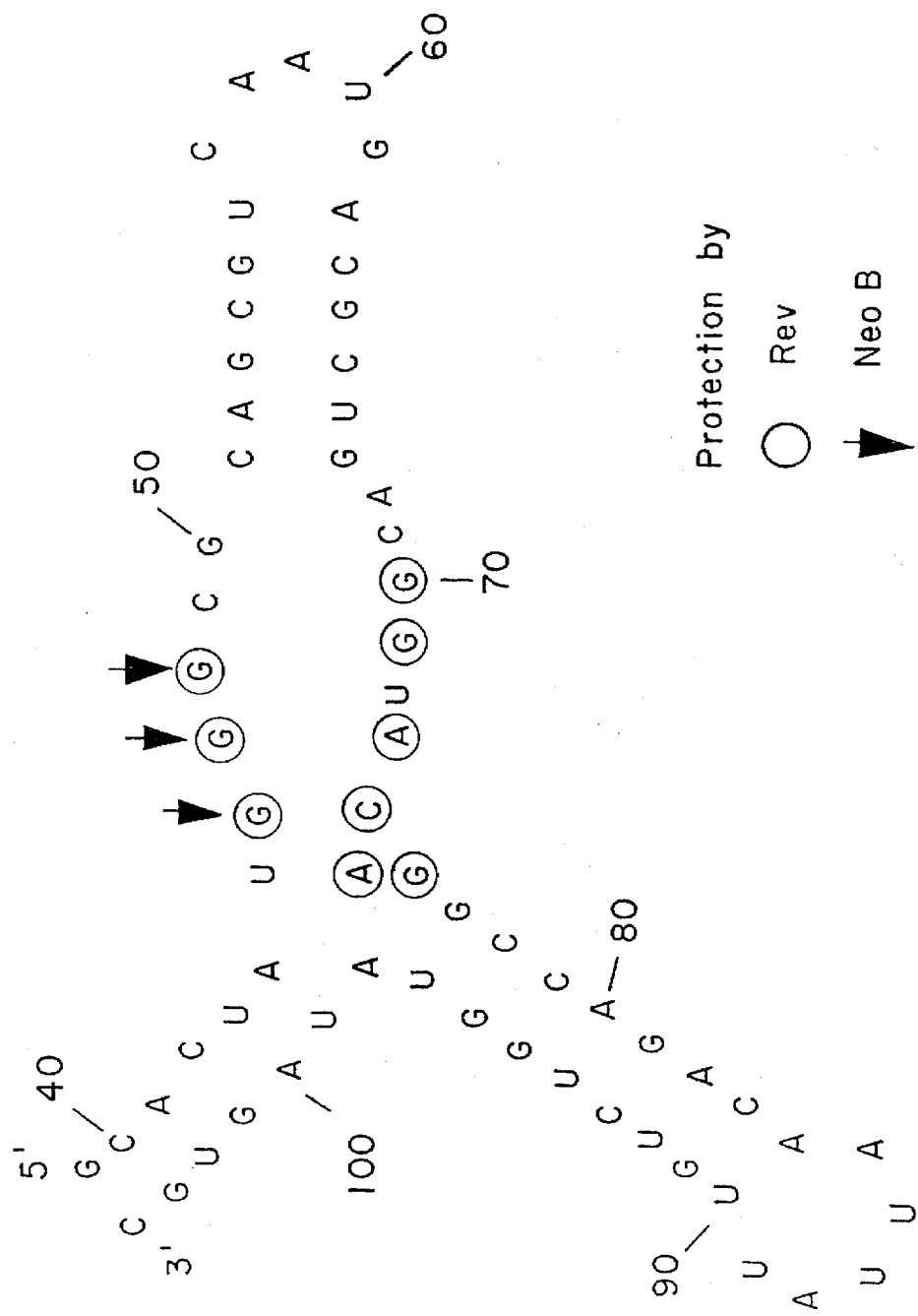
FIG. 3 is a schematic representation of the proposed secondary structure of the RRE sequence summarizing the results of the chemical protection experiments. Individual residues are shown which are protected from chemical modification by binding of Rev, and neomycin B.

The results (shown in FIG. 2) indicate that compound 15 inhibits Rev-RRE interaction in a concentration dependent fashion, with an IC$_{50}$ of 1.0 μM.

Example 35

Inhibition of Binding of Rev to RRE

Following the procedure of Example 34 the amidine compounds prepared in Examples 15 to 25 were tested for inhibition of binding of Rev to RRE. The results are summarized in Table 2 and Table 3.

TABLE 2

IC$_{50}$s of 2,5-Bis(3-amidinophenyl)furans against Rev/RRE binding

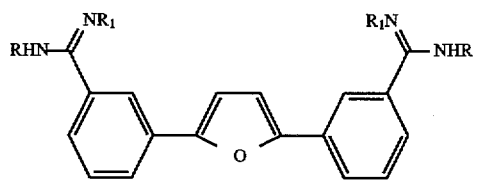

| Amidine | R$_1$ | R | IC$_{50}$ (μM) |
|---|---|---|---|
| Example 15 | H | Me$_2$N(CH$_2$)$_3$— | 1.0 |
| Example 16 | H | Et$_2$N(CH$_2$)$_3$— | 0.75 |
| Example 17 | H | Me$_2$N(CH$_2$)$_4$— | 1.7 |
| Example 18 | H | Me$_2$N(CH$_2$)$_6$— | 3.9 |
| Example 19 | | CH$_2$CH$_2$ | 4.0 |

TABLE 3

IC$_{50}$s of 2,5-Bis(3-bisamidinophenyl)thiophene against Rev/RRE binding

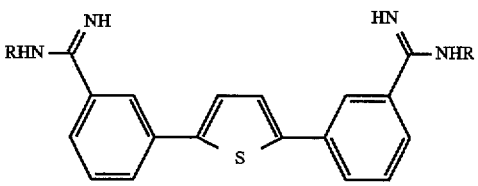

| Amidine | R | IC$_{50}$ (μM) |
|---|---|---|
| Example 20 | (3-ethylpyridyl) | not active |
| Example 21 | (1-methylpyrrolidinyl-propyl) | 2.4 |
| Example 22 | Et$_2$N~~~ | 2.8 |
| Example 23 | (pyrrolidinyl-ethyl) | not active |
| Example 24 | (morpholinyl) | not active |
| Example 25 | (piperidinyl-propyl) | 4.0 |

Example 36

Inhibition of Binding of Rev to RRE

Following the procedure of Example 34 the mixed amidine compounds prepared in Examples 26 to 33 were tested for inhibition of binding of Rev to RRE. The results are summarized in Table 4 and Table 5.

TABLE 4

IC$_{50}$s against Rev/RRE binding for
2,5-Bis(3-bisamidinophenyl)thiophenes from combinatorial synthesis using three amines

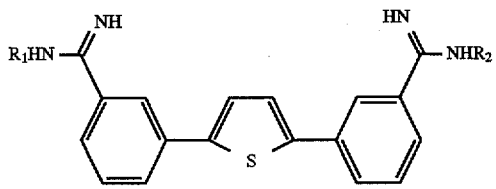

| Amidines | R$_1$ and R$_2$ | | | IC$_{50}$ (μM) |
|---|---|---|---|---|
| Example 26 | 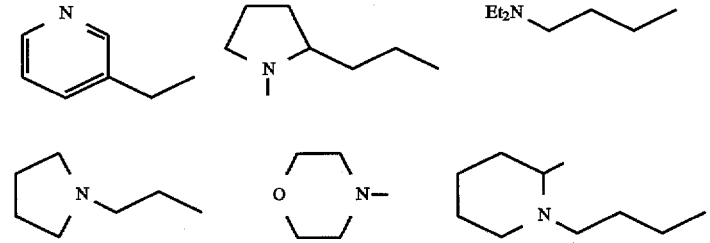 | | | 3.6 |
| Example 27 | 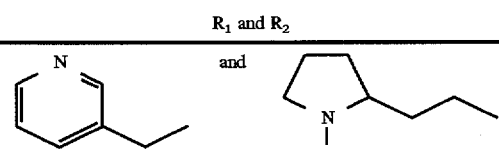 | | | 5.9 |

TABLE 5

IC$_{50}$s against Rev/RRE binding for
2,5-Bis(3-bisamidinophenyl)thiophenes from combinatorial synthesis using two amines

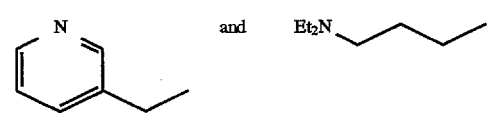

| Amidines | R$_1$ and R$_2$ | | IC$_{50}$ (μM) |
|---|---|---|---|
| Example 28 | | and | 0.81 |
| Example 29 | | and | 1.1 |
| Example 30 | | and | 0.81 |
| Example 31 | | and | 6.0 |
| Example 32 | | and | 1.3 |

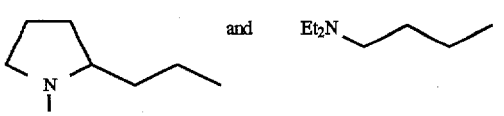
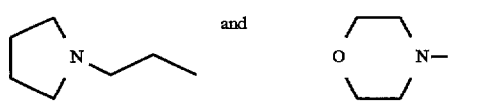
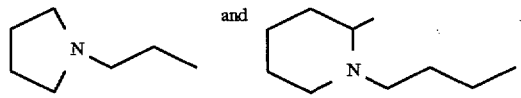

TABLE 5-continued

IC₅₀s against Rev/RRE binding for
2,5-Bis(3-bisamidinophenyl)thiophenes from combinatorial synthesis using two amines

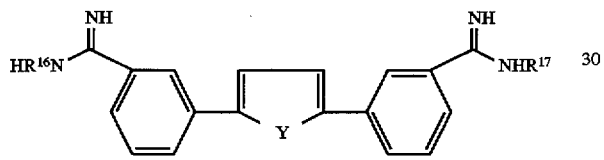

| Amidines | R₁ and R₂ | IC₅₀ (μM) |
|---|---|---|
| Example 33 | (morpholine) and (2-pentylpiperidine) | not active |

Many variations of the present invention will suggest themselves to those skilled in the art in light of the above detailed disclosure. All such modifications are within the full intended scope of the appended claims.

What is claimed is:

1. A compound having the formula:

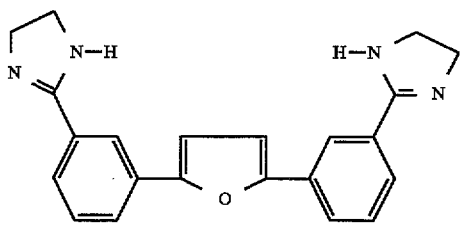

wherein Y is oxygen or sulfur;
wherein $R^{16}$ and $R^{17}$ are independently selected from the group consisting of hydrogen, $C_2$ to $C_7$ alkyl, and a heterocyclic ring having 3–10 ring atoms; wherein the heterocyclic ring is optionally substituted with $C_1$–$C_6$ alkyl groups;
wherein the hetero atoms are N, O, or S; and
wherein when $R^{16}$ and $R^{17}$ are alkyl groups, the alkyl groups are substituted with at least one radical selected from the group consisting of $C_1$ to $C_6$ dialkylamino, ($C_1$ to $C_6$ alkyl)(aryl)amino, di($C_1$–$C_6$ alkyl)amino($C_1$–$C_3$ alkyl)aryl, $C_3$–$C_8$ dicycloalkylamino, ($C_1$ to $C_6$ alkyl) ($C_3$–$C_8$ cycloalkyl)amino, and heterocyclic having 5 to about 7 ring atoms wherein the hetero atoms are N, O, or S; and
wherein $R^{16}$ and $R^{17}$ can be optionally interrupted by oxygen, nitrogen, sulfur, or any combination thereof; or a pharmaceutically acceptable salt thereof.

2. The compound according to claim 1 wherein Y is oxygen.

3. The compound according to claim 1 wherein Y is sulfur.

4. The compound according to claim 1 wherein $R^{16}$ or $R^{17}$ are independently selected from the group consisting of hydrogen, 3-N,N-dimethylaminopropyl, 4-N,N-dimethylaminobutyl, 6-N,N-dimethylaminohexyl, 3-pyridylmethyl, 2-(1-methyl-2-pyrrolidinyl)ethyl, 3-N,N-diethylaminopropyl, 2-pyrrolidinoethyl, (2-methylpiperidino)propyl; or an alkyl group having from about 3 to about 7 carbon atoms wherein said alkyl group is substituted with a dialkylamino group wherein said alkyl groups can each have from 1 to about 4 carbon atoms; or a pharmaceutically acceptable salt thereof.

5. The compound having the formula:

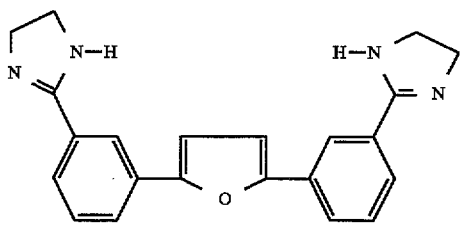

or a pharmaceutically acceptable salt thereof.

6. A compound having the formula:

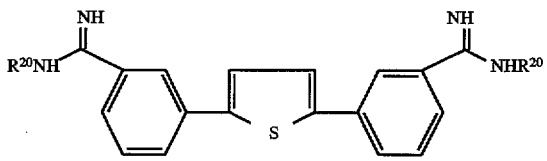

wherein each $R^{20}$ is independently an alkyl group having from about 3 to about 7 carbon atoms; wherein said alkyl group is substituted with a dialkylamino group in which each alkyl group has from 1 to about 4 carbon atoms; or a pharmaceutically acceptable salt thereof.

7. A compound having the formula:

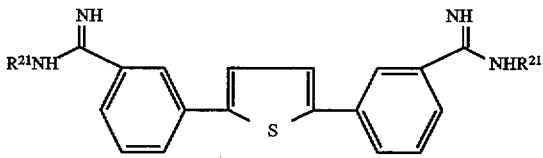

wherein each $R^{21}$ is independently an alkyl group having from about 3 to about 6 carbon atoms; wherein said alkyl group is substituted with a dialkylamino group in which each alkyl group has from 2 to about 4 carbon atoms, a 2-(1-methyl-2-pyrrolidinyl)ethyl group, or a 3-(2-methylpiperidino)propyl group; or a pharmaceutically acceptable salt thereof.

8. A compound having the formula:

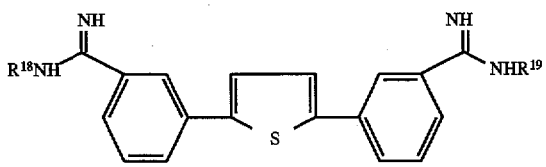

wherein R¹⁸ is 3-pyridylmethyl and R¹⁹ is 2-(1-methyl-2-pyrrolidinyl)ethyl or a pharmaceutically acceptable salt thereof.

9. A compound having the formula:

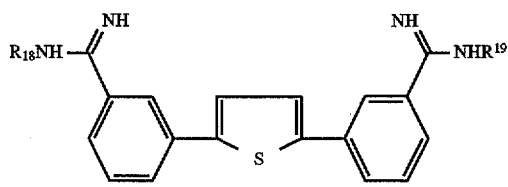

wherein R¹⁸ is 3-pyridylmethyl and R¹⁹ is 3-N,N-diethylaminopropyl, or R¹⁸ is 3-pyridylmethyl and R¹⁹ is an alkyl group having from about 3 to about 6 carbon atoms; wherein said alkyl group is substituted with a dialkylamino group in which each alkyl group has from 2 to about 4 carbon atoms; or a pharmaceutically acceptable salt thereof; and a pharmaceutically acceptable diluent or carrier.

10. A compound having the formula:

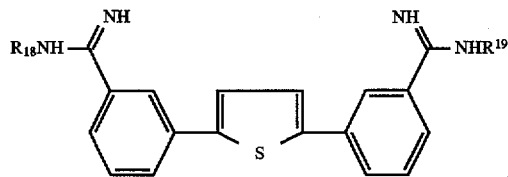

wherein R¹⁸ is 2-(1-methyl-2-pyrrolidinyl)ethyl and R¹⁹ is 3-N,N-diethylaminopropyl, or R¹⁸ is 2-(1-methyl-2-pyrrolidinyl)ethyl and R¹⁹ is an alkyl group having from about 3 to about 6 carbon atoms wherein said alkyl group is substituted with a dialkylamino group in which each alkyl group has from 2 to about 4 carbon atoms; or a pharmaceutically acceptable salt thereof.

11. A compound having the formula:

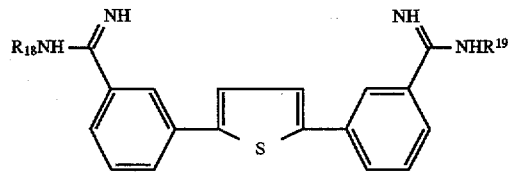

wherein R¹⁸ is 2-pyrrolidinoethyl and R¹⁹ is 3-(2-methylpiperidino)propyl or a pharmaceutically acceptable salt thereof.

12. A pharmaceutical composition comprising a compound having the formula:

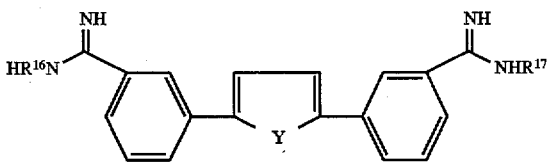

wherein Y is oxygen or sulfur;

wherein R¹⁶ and R¹⁷ are independently selected from the group consisting of hydrogen, C₂ to C₇ alkyl, and a heterocyclic ring having 3–10 ring atoms; wherein the heterocyclic ring is optionally substituted with C₁–C₆ alkyl groups;

wherein the hetero atoms are N, O, or S; and wherein when R¹⁶ and R¹⁷ are alkyl groups, the alkyl groups are substituted with at least one radical selected from the group consisting of C₁ to C₆ dialkylamino, (C₁ to C₆ alkyl)(aryl)amino, di(C₁14 C₆ alkyl)amino (C₁–C₆ alkyl)aryl, C₃–C₈ dicycloalkylamino, (C₁ to C₆ alkyl)(C₃–C₈ cycloalkyl)amino, and heterocyclic having 5 to about 7 ring atoms wherein the hetero atoms are N, O, or S; and wherein R¹⁶ and R¹⁷ can be optionally interrupted by oxygen, nitrogen, sulfur, or any combination thereof; or a pharmaceutically acceptable salt thereof; and a pharmaceutically acceptable diluent or earlier.

13. The composition according to claim 12, wherein Y is oxygen.

14. The composition according to claim 12, wherein Y is sulfur.

15. The composition according to claim 12, wherein R¹⁶ or R¹⁷ are independently selected from the group consisting of hydrogen, 3-N,N-dimethylaminopropyl, 4-N,N-dimethylaminobutyl, 6-N,N-dimethylaminohexyl, 3-pyridylmethyl, 2-(1-methyl-2-pyrrolidinyl)ethyl, 3-N,N-diethylaminopropyl, 2-pyrrolidinoethyl, (2-methylpiperidino) propyl; or an alkyl group having from about 3 to about 7 carbon atoms wherein said alkyl group is substituted with a dialkylamino group wherein said alkyl groups can each have from 1 to about 4 carbon atoms.

16. A pharmaceutical composition wherein the active ingredient is a compound having the formula:

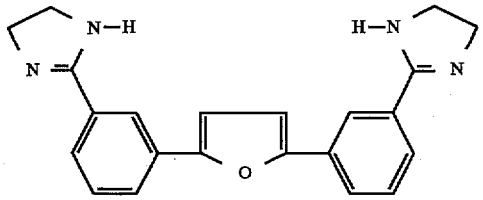

or a pharmaceutically acceptable salt thereof; and a pharmaceutically acceptable diluent or carrier.

17. A composition comprising a compound having the formula:

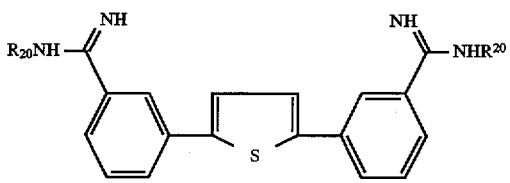

wherein each $R^{20}$ is independently an alkyl group having from about 3 to about 7 carbon atoms; wherein said alkyl group is substituted with a dialkylamino group in which each alkyl group has from 1 to about 4 carbon atoms; or a pharmaceutically acceptable salt thereof; and a pharmaceutically acceptable diluent or carrier.

18. A composition comprising a compound having the formula:

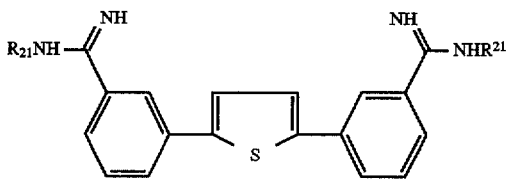

wherein each $R^{21}$ is independently an alkyl group having from about 3 to about 6 carbon atoms; wherein said alkyl group is substituted with a dialkylamino group in which each alkyl group has from 2 to about 4 carbon atoms, a 2-(1-methyl-2-pyrrolidinyl)ethyl group, or a 3-(2-methylpiperidino)propyl group; or a pharmaceutically acceptable salt thereof; and a pharmaceutically acceptable diluent or carrier.

19. A composition comprising a compound having the formula:

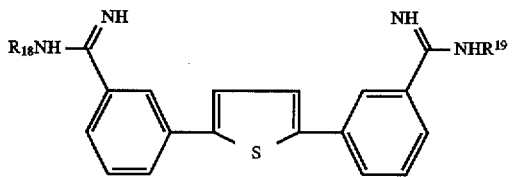

wherein $R^{18}$ is 3-pyridylmethyl and $R^{19}$ is 2-(1-methyl-2-pyrrolidinyl)ethyl or a pharmaceutically acceptable salt thereof; and a pharmaceutically acceptable diluent or carrier.

20. A composition comprising a compound having the formula:

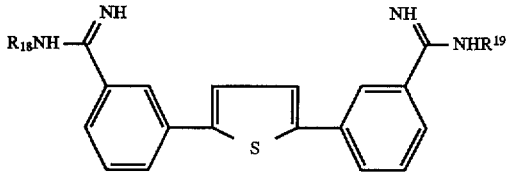

wherein $R^{18}$ is 3-pyridylmethyl and $R^{19}$ is 3-N,N-diethylaminopropyl, or $R^{18}$ is 3-pyridylmethyl and $R^{19}$ is an alkyl group having from about 3 to about 6 carbon atoms; wherein said alkyl group is substituted with a dialkylamino group in which each alkyl group has from 2 to about 4 carbon atoms; or a pharmaceutically acceptable salt thereof; and a pharmaceutically acceptable diluent or carrier.

21. A composition comprising a compound having the formula:

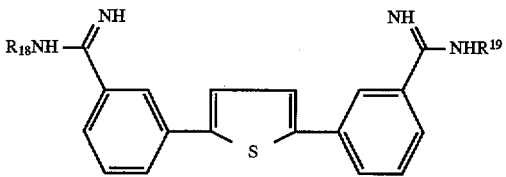

wherein $R^{18}$ is 2-(1-methyl-2-pyrrolidinyl)ethyl and $R^{19}$ is 3-N,N-diethylaminopropyl, or $R^{18}$ is 2-(1-methyl-2-pyrrolidinyl)ethyl and $R^{19}$ is an alkyl group having from about 3 to about 6 carbon atoms wherein said alkyl group is substituted with a dialkylamino group in which each alkyl group has from 2 to about 4 carbon atoms; or a pharmaceutically acceptable salt thereof; and a pharmaceutically acceptable diluent or carrier.

22. A composition comprising a compound having the formula:

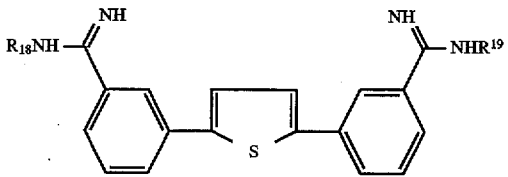

wherein $R^{18}$ is 2-pyrrolidinoethyl and $R^{19}$ is 3-(2-methylpiperidino)propyl or a pharmaceutically acceptable salt thereof; and a pharmaceutically acceptable diluent or carrier.

23. A method for inhibiting HIV Rev protein binding to RNA containing a Rev-responsive element, which comprises contacting the RNA with a compound having the formula:

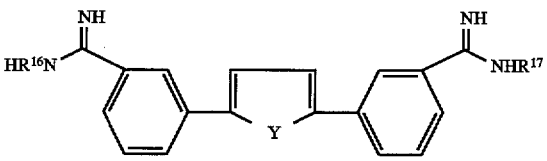

wherein Y is oxygen or sulfur;

wherein $R^{16}$ and $R^{17}$ are independently selected from the group consisting of hydrogen, $C_2$ to $C_7$ alkyl, and a heterocyclic ring having 3–10 ring atoms; wherein the heterocyclic ring is optionally substituted with $C_1$–$C_6$ alkyl groups;

wherein the hetero atoms are N, O, or S; and wherein when $R^{16}$ and $R^{17}$ are alkyl groups, the alkyl groups are substituted with at least one radical selected from the group consisting of $C_1$ to $C_6$ dialkylamino, ($C_1$ to $C_6$ alkyl)(aryl)amino, di($C_1$–$C_6$ alkyl)amino($C_1$–$C_3$ alkyl)aryl, $C_3$–$C_8$ dicycloalkylamino, ($C_1$ to $C_6$ alkyl)($C_3$–$C_8$ cycloalkyl)amino, and heterocyclic having 5 to about 7 ring atoms wherein the hetero atoms are N, O, or S; and wherein $R^{16}$ and $R^{17}$ can be optionally interrupted by oxygen, nitrogen, sulfur, or any combination thereof; or a pharmaceutically acceptable salt thereof, and a pharmaceutically acceptable diluent or carrier.

24. The method according to claim 23 wherein Y is oxygen.

25. A method for inhibiting HIV Rev protein binding to RNA containing a Rev-responsive element, which comprises contacting the RNA with a compound having the formula:

$$\text{HR}^{16}\text{N}\overset{\text{NH}}{\underset{}{\|}}\text{—}\underset{}{\text{(phenyl)}}\text{—}\underset{Y}{\text{(ring)}}\text{—}\underset{}{\text{(phenyl)}}\text{—}\overset{\text{NH}}{\underset{}{\|}}\text{NHR}^{17}$$

wherein Y is sulfur;

wherein $R^{16}$ and $R^{17}$ are independently selected from the group consisting of hydrogen, $C_2$ to $C_7$ alkyl, and a heterocyclic ring having 3–10 ring atoms; wherein the heterocyclic ring is optionally substituted with $C_1$–$C_6$ alkyl groups;

wherein the hetero atoms comprise N, and optionally O, or S; and wherein when $R^{16}$ and $R^{17}$ are alkyl groups, the alkyl groups are substituted with at least one radical selected from the group consisting of $C_1$ to $C_6$ dialkylamino, ($C_1$ to $C_6$ alkyl)(aryl)amino, di($C_1$–$C_6$ alkyl)amino($C_1$–$C_3$ alkyl)aryl, $C_3$–$C_8$ dicycloalkylamino, ($C_1$ to $C_6$ alkyl) ($C_3$–$C_8$ cycloalkyl)amino, and heterocyclic having 5 to about 7 ring atoms wherein the hetero atoms are N, O, or S; and wherein $R^{16}$ and $R^{17}$ can be optionally interrupted by oxygen, nitrogen, sulfur, or any combination thereof; or a pharmaceutically acceptable salt thereof, and a pharmaceutically acceptable diluent or carrier.

26. The method according to claim 23 wherein $R^{16}$ or $R^{17}$ are independently selected from the group consisting of hydrogen, 3-N,N-dimethylaminopropyl, 4-N,N-dimethylaminobutyl, 6-N,N-dimethylaminohexyl, 3-pyridylmethyl, 2-(1-methyl-2-pyrrolidinyl)ethyl, 3-N,N-diethylaminopropyl, 2-pyrrolidinoethyl, (2-methylpiperidino)propyl; or an alkyl group having from about 3 to about 7 carbon atoms wherein said alkyl group is substituted with a dialkylamino group wherein said alkyl groups can each have from 1 to about 4 carbon atoms.

27. A method for inhibiting RNA-protein interaction, which comprises contacting the RNA with a compound having the formula:

$$\text{HR}^{16}\text{N}\overset{\text{NH}}{\underset{}{\|}}\text{—}\underset{}{\text{(phenyl)}}\text{—}\underset{Y}{\text{(ring)}}\text{—}\underset{}{\text{(phenyl)}}\text{—}\overset{\text{NH}}{\underset{}{\|}}\text{NHR}^{17}$$

wherein Y is oxygen or sulfur;

wherein $R^{16}$ and $R^{17}$ are independently selected from the group consisting of hydrogen, $C_2$ to $C_7$ alkyl, and a heterocyclic ring having 3–10 ring atoms; wherein the heterocyclic ring is optionally substituted with $C_1$–$C_6$ alkyl groups;

wherein the hetero atoms are N, O, or S; and wherein when $R^{16}$ and $R^{17}$ are alkyl groups, the alkyl groups are substituted with at least one radical selected from the group consisting of $C_1$ to $C_6$ dialkylamino, ($C_1$ to $C_6$ alkyl)(aryl)amino, di($C_1$–$C_6$ alkyl)amino($C_1$–$C_3$ alkyl)aryl, $C_3$–$C_8$ dicycloalkylamino, ($C_1$ to $C_6$ alkyl) ($C_3$–$C_8$ cycloalkyl)amino, and heterocyclic having 5 to about 7 ring atoms wherein the hetero atoms are N, O, or S; and wherein $R^{16}$ and $R^{17}$ can be optionally interrupted by oxygen, nitrogen, sulfur, or any combination thereof; or a pharmaceutically acceptable salt thereof, and a pharmaceutically acceptable diluent or carrier.

28. The method of according to claim 27, wherein $R^{16}$ or $R^{17}$ are independently selected from the group consisting of hydrogen, 3-N,N-dimethylaminopropyl, 4-N,N-dimethylaminobutyl, 6-N,N-dimethylaminohexyl, 3-pyridylmethyl, 2-(1-methyl-2-pyrrolidinyl)ethyl, 3-N,N-diethylaminopropyl, 2-pyrrolidinoethyl, 2-(methylpiperidino)propyl; or an alkyl group having from about 3 to about 7 carbon atoms wherein said alkyl group is substituted with a dialkylamino group wherein said alkyl groups can each have from 1 to about 4 carbon atoms.

29. A method of inhibiting retroviral replication in a cell infected with a retrovirus, which comprises contacting said retroviral-infected cell with a compound having the formula:

$$\text{HR}^{16}\text{N}\overset{\text{NH}}{\underset{}{\|}}\text{—}\underset{}{\text{(phenyl)}}\text{—}\underset{Y}{\text{(ring)}}\text{—}\underset{}{\text{(phenyl)}}\text{—}\overset{\text{NH}}{\underset{}{\|}}\text{NHR}^{17}$$

wherein Y is oxygen or sulfur;

wherein $R^{16}$ and $R^{17}$ are independently selected from the group consisting of hydrogen, $C_2$ to $C_7$ alkyl, and a heterocyclic ring having 3–10 ring atoms; wherein the heterocyclic ring is optionally substituted with $C_1$–$C_6$ alkyl groups;

wherein the hetero atoms are N, O, or S; and wherein when $R^{16}$ and $R^{17}$ are alkyl groups, the alkyl groups are substituted with at least one radical selected from the group consisting of $C_1$ to $C_6$ dialkylamino, ($C_1$ to $C_6$ alkyl)(aryl)amino, di($C_1$–$C_6$ alkyl)amino($C_1$–$C_3$ alkyl)aryl, $C_3$–$C_8$ dicycloalkylamino, ($C_1$ to $C_6$ alkyl) ($C_3$–$C_8$ cycloalkyl)amino, and heterocyclic having 5 to about 7 ring atoms wherein the hetero atoms are N, O, or S; and wherein $R^{16}$ and $R^{17}$ can be optionally interrupted by oxygen, nitrogen, sulfur, or any combination thereof; or a pharmaceutically acceptable salt thereof, and a pharmaceutically acceptable diluent or carrier.

30. The method of according to claim 29, wherein $R^{16}$ or $R^{17}$ are independently selected from the group consisting of hydrogen, 3-N,N-dimethylaminopropyl, 4-N,N-dimethylaminobutyl, 6-N,N-dimethylaminohexyl, 3-pyridylmethyl, 2-(1-methyl-2-pyrrolidinyl)ethyl, 3-N,N-diethylaminopropyl, 2-pyrrolidinoethyl, 2-(methylpiperidino)propyl; or an alkyl group having from about 3 to about 7 carbon atoms wherein said alkyl group is substituted with a dialkylamino group wherein said alkyl groups can each have from 1 to about 4 carbon atoms.

31. The method according to claim 29, wherein the retrovirus is HIV, the retroviral-encoded RNA comprises a Rev-responsive element and the binding protein is Rev.

32. The compound according to claim 4 wherein the 2-methylpiperidinopropyl group is 3-(2-methylpiperidino) propyl.

33. The composition according to claim 15 wherein the 2-methylpiperidinopropyl group is 3-(2-methylpiperidino) propyl.

34. The method according to claim 26 wherein the 2-methylpiperidinopropyl group is 3-(2-methylpiperidino) propyl.

35. The method according to claim 28 wherein the 2-methylpiperidinopropyl group is 3-(2-methylpiperidino) propyl.

36. The method according to claim 30 wherein the 2-methylpiperidinopropyl group is 3-(2-methylpiperidino) propyl.

* * * * *